United States Patent
Umezawa et al.

[11] Patent Number: 5,985,674
[45] Date of Patent: Nov. 16, 1999

[54] EVALUATION METHOD FOR CLEANLINESS OF METAL

[75] Inventors: Kazushige Umezawa, Futtsu; Tokio Suzuki; Koichi Chiba, both of Kawasaki; Ryuji Uemori; Takehiko Toh, both of Futtsu; Hiroyuki Kondo, Kawasaki; Katsuhiro Fuchigami, Oita; Eiichi Takeuchi, Futtsu; Masamitsu Wakoh, Oita; Akihiro Ono, Kawasaki, all of Japan

[73] Assignee: Nippon Steel Corporation, Tokyo, Japan

[21] Appl. No.: 08/737,839

[22] PCT Filed: Mar. 14, 1996

[86] PCT No.: PCT/JP96/00650

§ 371 Date: Dec. 13, 1996

§ 102(e) Date: Dec. 13, 1996

[87] PCT Pub. No.: WO96/28729

PCT Pub. Date: Sep. 19, 1996

[30] Foreign Application Priority Data

| Mar. 14, 1995 | [JP] | Japan | 7-054810 |
| Mar. 24, 1995 | [JP] | Japan | 7-066592 |
| May 18, 1995 | [JP] | Japan | 7-142456 |
| Jan. 29, 1996 | [JP] | Japan | 8-012369 |
| Jan. 29, 1996 | [JP] | Japan | 8-012370 |
| Feb. 7, 1996 | [JP] | Japan | 8-021272 |
| Feb. 7, 1996 | [JP] | Japan | 8-021273 |
| May 19, 1999 | [JP] | Japan | 7-121786 |

[51] Int. Cl.$^6$ .................................................. G01N 21/64
[52] U.S. Cl. .......................... 436/172; 436/73; 436/78; 436/127; 436/177; 148/508; 378/45
[58] Field of Search ............................ 436/73, 78, 127, 436/172, 177; 378/44, 45, 47, 49; 250/483.1; 219/648; 164/493, 467; 148/508, 538

[56] References Cited

U.S. PATENT DOCUMENTS

| 3,432,753 | 3/1969 | Horn . |
| 4,329,136 | 5/1982 | Willay et al. . |

(List continued on next page.)

FOREIGN PATENT DOCUMENTS

| 166346 | 1/1986 | European Pat. Off. . |
| 2 549 735 | 11/1977 | Germany . |

(List continued on next page.)

OTHER PUBLICATIONS

Chemical Abstracts CA89: 156874, Pauwels, Comm. Eur. Communities, [Rep.] Eur (1978), Eur 5916, 39 pp.

Chemical Abstracts CA 125: 206699, Matyunin et al. Proc. Embedded Top Meet. DOE Spent Nucl. Fuel Fissile Mater. Munaga. (1996), 201–205. Publisher: American Nuclear Society, La Grange Park, Ill.

*Primary Examiner*—Jan Ludlow
*Attorney, Agent, or Firm*—Kenyon & Kenyon

[57] ABSTRACT

In order to quickly and economically evaluate cleanliness of a metal with high representativity when quantities, compositions, etc., of non-metallic inclusion particles existing in a metal and resulting in product defects are evaluated by a sample collected during the production process of the metal, the present invention provides an evaluation method involving the steps of levitation-melting a metal piece for a predetermined time by cold crucible levitation-melting means, discharging non-metallic inclusion particles contained in the metal piece to the surface of a molten metal, and directly analyzing a curved and non-smooth sample surface after solidification by a fluorescent X-ray analysis method using an energy dispersion type spectroscope, or by other chemical or physical measurements, to measure or analyze the quantities of elements constituting the non-metallic inclusion particles and to determine quantity of the non-metallic inclusions.

2 Claims, 19 Drawing Sheets

U.S. PATENT DOCUMENTS

| | | |
|---|---|---|
| 4,612,042 | 9/1986 | Kelly et al. . |
| 4,680,716 | 7/1987 | Naudi . |
| 5,058,127 | 10/1991 | Garnier et al. . |
| 5,257,302 | 10/1993 | Narukawa . |
| 5,269,827 | 12/1993 | Lenke et al. . |
| 5,315,091 | 5/1994 | O'Brien et al. . |
| 5,427,952 | 6/1995 | Daugherty et al. . |

FOREIGN PATENT DOCUMENTS

| | | |
|---|---|---|
| 49-7197 | 2/1974 | Japan . |
| 58-172596 | 10/1983 | Japan . |
| 2-216444 | 8/1990 | Japan . |
| 5-346387 | 12/1993 | Japan . |
| 7-239327 | 9/1995 | Japan . |

CASTING DIRECTION

EVALUATION METHOD FOR CLEANLINESS OF METAL

TECHNICAL FIELD

In conjunction with non-metallic inclusions contained in a metal, the present invention relates to an evaluation apparatus for cleanliness of a metal, and a method therefor, which quickly discharges non-metallic inclusions contained in a steel, for example, to the surface portion, detects the non-metallic inclusions accumulating the surface either chemically or physically, and accurately determines the proportion of the non-metallic inclusions in the metal as a total quantity evaluation or as an evaluation of principal components in accordance with a particle size distribution.

BACKGROUND ART

Hereinafter, the explanation will be given using steel as a typical example of a metal. Non-metallic inclusion particles existing in the steel include alumina type inclusions formed as the result of the reaction between oxygen in the steel and aluminum added in the case of an aluminum killed steel, slag type inclusions containing lime/silica, etc., and resulting from a steel making slag, powder type inclusions resulting from a casting mold lubricant in continuous casting, and so forth. Since these inclusions result in defects such as flows and breakage in intermediate products, during rolling of thin sheets, wire materials, etc., or in final products, evaluation of these inclusions by various methods have bean carried out in the past for the purpose of quality control.

If any defects are found in the final product, on the other hand, it is a serious problem to discard the product at the final stage from the aspect of the production cost because the product is produced through various production steps. It is therefore desirable to evaluate quality at an early stage of the production. Particularly because the existence of the inclusions is determined at the stage of refining/solidification of the metal, various evaluation technologies have been conducted in the past.

The evaluation technology of the inclusions of the steel among the metals is described, for example, in "Steel Handbook, 3rd Edition", II Pig Iron & Steel Making (edited by Japan Iron & Steel Institute of Japan, published by Maruzen, Oct. 15, 1979). Examples of the evaluation methods include a total oxygen (T[O]) method based on the oxygen concentration in the steel, a slime method by electrolytic extraction used for evaluating large inclusions, a microscopic method for evaluating the inclusions by magnifying and observing the section of a metal, and so forth. Due to their respective features, these technologies are limited by the kind of inclusions as the investigation object and the sizes of the inclusions as tabulated in Table 1, and they are not free from the problem, either, that a long time is necessary depending on the evaluation method.

It is known that information of intermediate products is not sufficient so as to estimate the product defects. In other words, as shown in Table 1, the conventional means involves the problems that the evaluation sample does not sufficiently represent the quality of the intermediate product and a long time is necessary for the evaluation of the sample, and those methods which invite excessively great super-heat during melting such as an EB (electron beam melting) method involve the problem that the inclusions are denatured during evaluation.

The slime method has been widely employed as a method having relatively high accuracy, but an extremely long time of several days to dozens of days is necessary to electrolyze about 1 kg sample as a whole.

When the evaluation is made by a small amount of metal sample, a metal piece sample of a part of large amounts of metal is evaluated. Therefore, to strictly evaluate the cleanliness of the whole metal, a large number of samples must be collected from the same metal piece, and the problem to be solved is to speed up the evaluation of the cleanliness.

TABLE 1

| name | particle diameter of inclusions | evaluation quantity & necessary time | others |
| --- | --- | --- | --- |
| microscope | up to 40 μm | 100 positions, 25 mm² several days | |
| T[O] | — | — | |
| slime | at least 40 μm | several kg, several to dozens of days | |
| EB | up to 200 μm | 2 g (several pcs) one day | components evaporate due to reduced pressure |
| This Invention | not limited | hundred to thousand grams, about 10 min. | components do not evaporate due to Ar atmospheric pressure |

On the other hand, though the melting means is different from the EB method, an induction melting extraction method using a cold crucible method is conceivable as the same melting extraction method. In other words, this method eliminates the problems such as high temperature melting of the EB method and the resulting modification of the inclusions, and insufficiency as the representative value by the evaluation volume of the small amount. A method of measuring the inclusions of the surface of the sample produced by this cold crucible levitation-melting method is described, for example, in "Evaluation of Alloy Cleanness in Superclean Materials", K. C. Mills et al., Turkdogan Symposium Proceedings, pp. 105–112 (1994). The method of this reference inspects the surface inclusions by a scanning electron microscope. However, this reference points out only the problem as the evaluation method by the characteristics of the cold crucible itself, but does not teach the method of evaluating the non-metallic inclusions over a wide area of the metal surface industrially, economically and quickly.

FIGS. 1(a) and 1(b) are explanatory views of the principal portions of a cold crucible apparatus, wherein FIG. 1(a) is an explanatory plan view, and FIG. 1(b) is an explanatory view of the longitudinal section taken along A—A of FIG. 1(a). In FIG. 1, reference numerals (1-1, . . . , 1-8) denote eight, for example, copper segments which together form a crucible and the inside of which is cooled with water. They are disposed adjacent to one another with the gap slits 3 interposed at a plurality of substantially equidistant positions and form the crucible. Reference numeral 2 in the drawings denotes an induction coil, which is so disposed as to encompass the crucible.

FIGS. 2(a) and 2(b) are explanatory views of the operation of the cold crucible. When a high frequency current flows through the induction coil 2 in a direction indicated by an arrow 5, an inducted electromotive force occurs in a direction indicated by an arrow 6-1 occurs on the side of the induction coil 2 of the segments 1. Since the segments 1 are spaced apart from one another by the slits 3, however, the induction current does not flow through other adjacent segments, but flows as an induction current in a direction indicated by an arrow 6-2 on the opposite side to the induction coil. Reference numeral 4 in the drawing represents the metal sample. An eddy current flows through the metal sample 4 in a direction indicated by an arrow 7 due to the induction current in a direction indicated by an arrow 6-2. The metal piece 4 is heated by the eddy current in the direction of the arrow 7 and is melted. In this instance, since the eddy current flows through the molten metal 4 in the direction of the arrow 7, repulsion 8 acts in the center direction of the metal due to the induction current in the direction of the arrow 6-2 that flows through the segments 1, and this repulsion 8 keeps the molten metal 4, under a levitating and non-contact state, away from the segments 1.

The cold crucible method melts the metal sample, due to levitation, in a non-oxidizing atmosphere and holds the levitating molten metal. During this retention time, the non-metallic inclusions in the metal sample are discharged to the surface of the molten metal as indicated by reference numeral 9 in FIG. 2(b). When the current to be passed through the coil is cut off after retention for a predetermined time, the molten metal is solidified while the non-metallic inclusions gather on the surface thereof. The cleanliness of the metal piece is evaluated by measuring the non-metallic inclusions gathered on the surface of the solidified body.

According to the prior art method which measures the non-metallic inclusions scattered inside the metal piece, measurement is complicated and requires a long measurement time but according to the cold crucible method, the measurement of the non-metallic inclusions gathering on the surface can be easily made because they gather on the surface of the solidified body and, moreover, within a short time. According to the prior art method which measures the non-metallic inclusions contained and scattered in the metal, the sample is extremely small, and is not correct as a representative value of the steel. On the other hand, because the cold crucible method can levitate several grams to several kilograms of the metal sample, the quantity of the sample is greater than before, and evaluation can be made more correctly over a typical values of the steel.

SUMMARY OF THE INVENTION

If the quality of intermediate products corresponding to quality of products of metal pieces can be quickly evaluated as compared to the prior art, the production cost and time can be drastically improved. The present invention is completed on the basis of this concept.

In other words, the present invention is directed to solve the problems of representativity of the evaluation samples in quality evaluation of the intermediate products, the problems of the measurement time and cost, and the problem of denaturing of inclusions. If the cold crucible treatment alone is merely carried out and the non-metallic inclusions are merely gathered on the sample surface, it takes a long time to investigate the surface by using the microscope and to count the number of the non-metallic inclusions, as described in the reference described above, and the intended objects cannot be accomplished.

To accomplish the objects described above, the present invention provides an apparatus, and a method therefor, which can gather non-metallic inclusions to the most advantageous position for the measurement of the whole quantity by a cold crucible, and can efficiently measure the whole quantity.

The gist of the present invention resides in the following points.

(1) An evaluation apparatus for cleanliness of a metal, comprising: metal levitation-melting means which comprises a water-cooled metal crucible including a bottom surface having a curvature and a sidewall surface having a sloped surface gradually expanding upward, and having slits interposed in a radial direction, an induction coil for generating a repulsion from the sidewall surface of the water-cooled metal crucible to a center direction, and passing a high frequency current for melting the metal while levitating the metal, and a container for maintaining a non-oxidizing atmosphere; handling means for taking out a metal having non-metallic inclusions accumulating at a specific position on the surface of the metal melted and solidified inside the metal levitation-melting means, and transferring the metal to analyzing means; and the analyzing means for analyzing the non-metallic inclusions so accumulated.

(2) An evaluation apparatus for cleanliness of a metal according to the item (1), comprising: metal levitation-melting means which comprises a water-cooled metal crucible comprising a plurality of segments divided in a circumferential direction, and having an open upper surface and a closed lower surface, an induction coil for passing a high frequency current, disposed in such a manner as to encompass the water-cooled metal crucible, and a non-oxidizing atmosphere container; handling means for taking out a metal melted and solidified by the levitation-melting means from the water-cooled metal crucible, moving the metal, and capable of setting the metal to a predetermined analysis position; and energy dispersion type fluorescent X-ray means for analyzing non-metallic inclusions accumulating on the surface of the metal.

(3) An evaluation apparatus for cleanliness of a metal according to the item (1), comprising: metal levitation-melting means which comprises a water-cooled metal crucible comprising a plurality of segments divided in a circumferential direction, and having an open upper surface and a closed lower surface, an induction coil for passing a high frequency current, disposed in such a manner as to encompass the water-cooled metal crucible, and a non-oxidizing atmosphere container; metal transferring means for taking out a metal melted and solidified by the levitation-melting means from the water-cooled metal crucible, and transferring the metal to predetermined processing means; and acid-dissolving or electrolyzing means for extracting non-metallic inclusions concentrated on the surface of the metal melted and solidified by the processing means.

(4) An evaluation apparatus for cleanliness of a metal according to the item (1), comprising: metal-levitation means which comprises a water-cooled metal crucible comprising a plurality of segments divided in a circumferential direction, and having an open upper surface and a closed lower surface, an induction coil for passing a high frequency three-phase alternating current for imparting a repulsion moving upward on the surface of a molten metal along the wall of the crucible while levitating and melting the metal thereinside, disposed in such a manner as to encompass the water-cooled metal crucible; and luminance difference/area conversion means for analyzing non-metallic inclusions accumulating on the upper surface of the metal melted and solidified by the levitation-melting means.

(5) An evaluation apparatus for cleanliness of a metal according to the item (1), wherein means for supplying a current to be passed through the induction coil is a single-phase alternating current source.

(6) An evaluation apparatus for cleanliness of a metal according to any of the items (2) through (4), wherein the shape of the inner surface of the crucible has a shape formed by cutting a rotating body having the symmetry axis of a perpendicular axis into halves on a plane of symmetry, and a shape formed by an upper shape of a circular truncated cone having the same shape as that of the symmetry plane or an upwardly expanded similar shape of the horizontal section.

(7) An evaluation apparatus for cleanliness of a metal according to any of the items (2) through (4), wherein the bottom surface of the crucible is shaped in such a manner that the bottom of the inner surface in an area of at least 90% by the diameter of the inner surface becomes a flat surface.

(8) An evaluation method for cleanliness of a metal comprising the steps of: levitation-melting a metal piece for a predetermined time by using levitation-melting means; discharging non-metallic inclusions contained in the metal piece to the surface of a molten metal; and directly analyzing a curved and non-smooth surface of the metal after solidification by a fluorescent X-ray analysis means using an energy dispersion type spectroscope so as to measure quantities of elements constituting the non-metallic inclusions and to identify the quantity of the non-metallic inclusions.

(9) An evaluation method for cleanliness of a metal according to the item (8), comprising the steps of: levitation-melting a metal piece for a predetermined time by using levitation-melting means; discharging non-metallic inclusions contained in the metal piece to the surface of a molten metal; rotating either intermittently or continuously the metal having a curved and non-smooth surface round an axis connecting the uppermost point and the lowermost point at the time of melting as the center thereof; directly analyzing the surface of the metal by a fluorescent X-ray analysis means using an energy dispersion type spectroscope; measuring the quantities of elements constituting the non-metallic inclusions; and identifying the quantities of the non-metallic inclusions in accordance with the kind or the origin.

(10) An evaluation method for cleanliness of a metal comprising the steps of: levitation-melting a metal piece for a predetermined time by using levitation-melting means; discharging non-metallic inclusions contained in the metal piece to the surface of a molten metal; dissolving the surface of the metal after solidification by an acidic solution or electrolyzing it in an aqueous type solution or a non-aqueous type solution; extracting and filtrating the non-metallic inclusions; and weighing and analyzing the non-metallic inclusions so filtrated, or weighing and analyzing them after separation.

(11) An evaluation method for cleanliness of a metal according to the item (10), wherein the retention time t (seconds) of the levitation-melted metal for accumulating the non-metallic inclusions contained in the metal to the surface of the levitation-melted metal falls within the following range (1):

$$1 \leq t/\sqrt{(30d)} \leq 20 \tag{1}$$

where d is a maximum inner diameter (mm) of the crucible.

(12) An evaluation method for cleanliness of a metal characterized in that measurement of non-metallic inclusions accumulating on the surface of the top of a molten metal is carried out by the steps of cutting off a high frequency current after a metal sample is levitation-melted, the difference of luminance between the surface of the metal sample during cooling and the non-metallic inclusions is photographed by a CCD camera, and island-like occupying areas of the non-metallic inclusions are measured by image processing the image so photographed.

(13) An evaluation method for cleanliness of a metal according to the item (11), comprising the steps of: carrying out a levitation-melting treatment by changing $t/\sqrt{(30\ d)}$ (t: retention time of a levitation-melted metal (seconds), d: maximum inner diameter (mm) of crucible); determining in advance the relation between $t/\sqrt{(30\ d)}$ and a diameter L of the non-metallic inclusions by investigating the diameter L occurring at maximum frequency at each $t/\sqrt{(30\ d)}$ value; selecting a desired value for $t/\sqrt{(30\ d)}$ when the cleanliness of another metal is evaluated, and carrying out the levitation-melting treatment for the other metal; measuring the occurring quantity N of the non-metallic inclusions having the diameter L in the other metal by estimating that the diameter L of the non-metallic inclusions occurring at the maximum frequency in the other metal at this selected $t/\sqrt{(30\ d)}$ value is the same as the relation that is determined in advance; and evaluating this N as cleanliness of the other metal.

(14) An evaluation method for cleanliness of a metal according to the item (13), wherein the occurring quantities $N_1, N_2, \ldots$ of the non-metallic inclusions having diameters $L_1, L_2, \ldots$ greater than L are measured in the other metal, and the $N_1, L_2, \ldots$ values are evaluated as cleanliness of the other metal.

(15) An evaluation method for cleanliness of a metal according to the item (10), wherein at least 10 particles are selected from particles having the maximum diameter in the non-metallic inclusions discharged, and the diameters of the non-metallic inclusions having the maximum particle diameters existing in the metal from which the metal piece is collected, are estimated by a statistical extremes method.

BEST MODE FOR CARRYING OUT THE INVENTION

To efficiently detect the whole quantity of non-metallic inclusions of a sample, the present invention carries out levitation-melting so that the aggregate of non-metallic inclusions to be discharged can be controlled to an optimum position of the sample. In this way, the discharge and aggregate position can be set easily and quickly to the position at which analysis by an energy dispersion type fluorescent X-ray apparatus can be executed. When the non-metallic inclusions can be aggregated near the center of the upper surface of the sample surface portion, the set position can be positioned to the X-ray visual field. When they are aggregated to the center of the side surface, the non-metallic inclusions so aggregated can be efficiently analyzed by rotating the X-ray source. The characterizing feature of the present invention resides in that cleanliness of metals can be evaluated economically and quickly with high reproducibility.

Hereinafter, a concrete construction of the method of the present invention will be described with reference to FIG. 3.

Figure 1A:
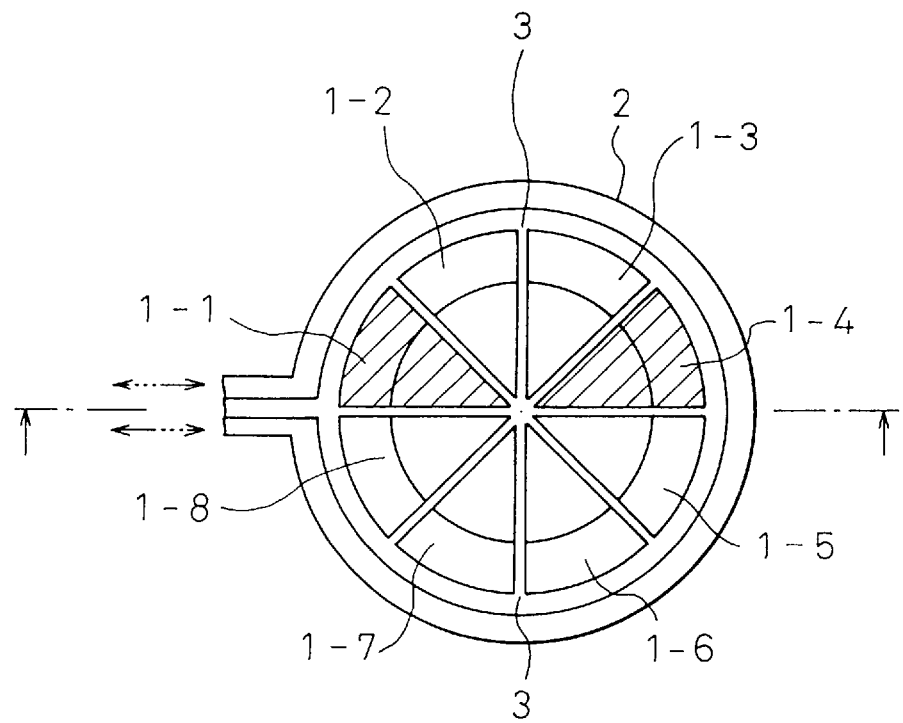
FIG. 1(a) is an explanatory view of principal portions of a cold crucible apparatus.
Figure 1B:
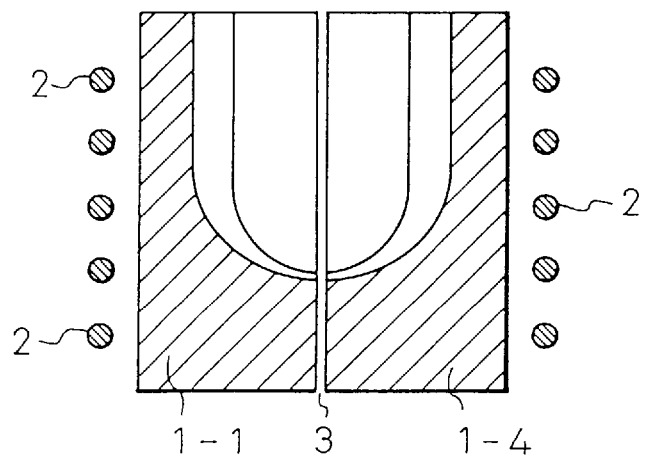
FIG. 1(b) is a longitudinal section view taken along a line A—A of FIG. 1(a).
Figure 2A:
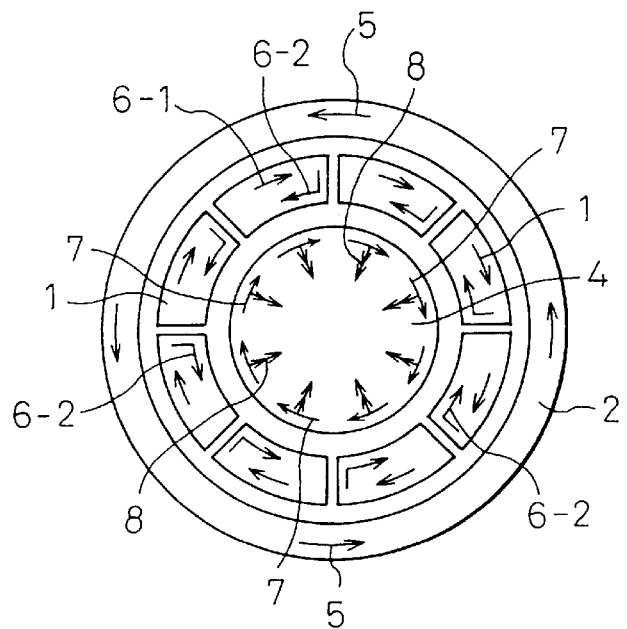
FIG. 2(a) is an explanatory view of the operation of the cold crucible.
Figure 2B:
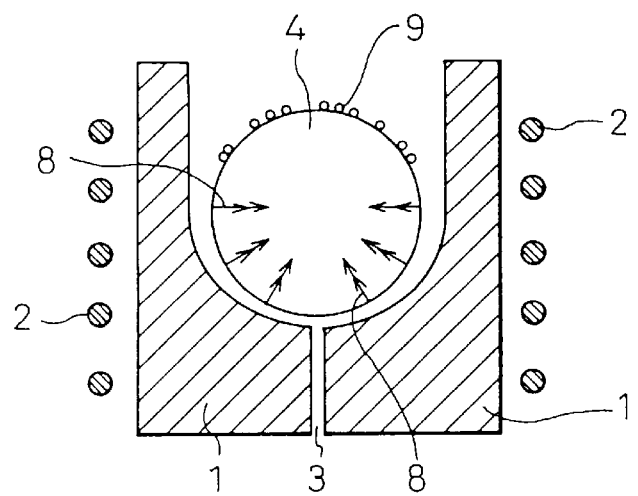
FIG. 2(b) is a longitudinal sectional view of FIG. 2(a).
Figure 4:
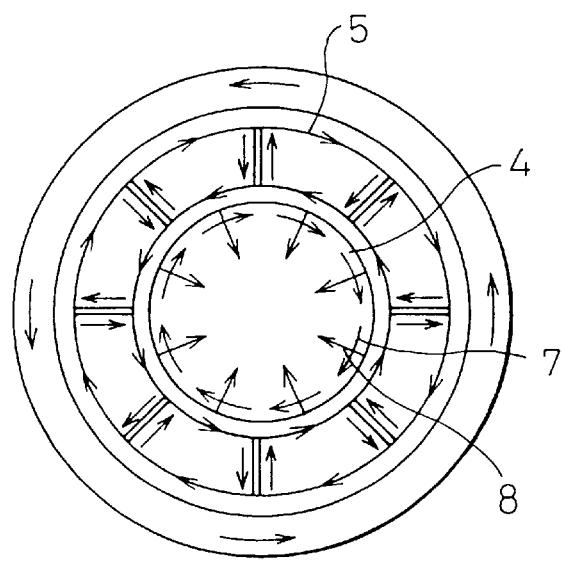
FIG. 4 is an explanatory view showing the flows of a high frequency current and an eddy current.
Figure 9:
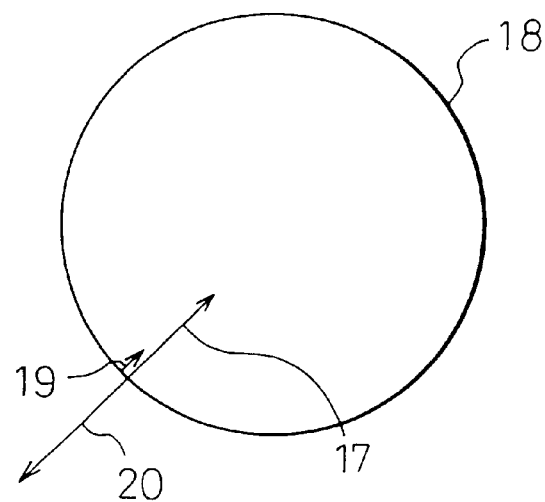
FIG. 9 is a view showing the relation between an electromagnetic force acting on a molten metal and surface tension, etc.

A metal crucible (cold crucible) 13 comprising metal segments 1 divided in a circumferential direction and having an open upper surface and a closed lower surface as shown in FIG. 2(a) is disposed inside a container 11 capable of controlling an inert gas atmosphere or a vacuum atmosphere 10 as a non-oxidizing atmosphere. The shape of this crucible may be such that its bottom surface has a curvature and its sidewall surface has an inclination so that the inner diameter progressively increases towards the upper portion. The crucible is encompassed by a water cooled coil 16 through which a high frequency current 15 given by a high frequency transmitter 14 is caused to flow. A metal sample 6 as an object whose weight is measured in advance is placed inside the crucible and then the current is caused to flow through the coil. Then, the molten metal 6 levitates inside the water cooled metal crucible 13 due to the resulting electromagnetic force 17. FIG. 4 is an explanatory view of the flows of the high frequency current and an induction current at this time. When the high frequency current flows through the induction coil, induction electromotive force 5 develops on the induction coil side of the segments. Since the segments are mutually separated by the slits, however, the induction current does not flow through the adjacent segments but flows as the induction current on the opposite side of the high frequency coil of the segments. An eddy current 7 flows through the metal sample due to the induction current. The metal piece is heated and melted by this eddy current 7. In this instance, because the eddy current flows through the molten metal, repulsion 8 operates in the center direction of the metal due to the induction current flowing through the segment, and this repulsion 8 keeps the molten metal in the levitated state while it is out of contact with the segments. Because the sectional area of the inside of the crucible progressively decreases towards the lower portion, a stronger electromagnetic force acts on the metal at a lower portion. In consequence, the balance of the electromagnetic force 17, surface tension 19 and gravity 20 is established at the time of melting as shown in FIG. 9, and the molten metal levitates inside the crucible. The specific gravities of the non-metallic inclusions are smaller than that of the molten metal, the reaction to the push force of the induced electromagnetic force that pushes inward the molten metal acts on the non-metallic inclusions and furthermore, surface tension exists between the non-metallic inclusions and the molten metal. Therefore, the levitation melted body is discharged to the outer periphery 18. After retention for a predetermined time, the electric current through the coil is cut off. Then, the molten metal is solidified, and the non-metallic inclusions accumulate on the surface of the levitation melted body.

The present invention comprises an invention for accumulating the non-metallic inclusions discharged to the surface to a position at which evaluation can be quickly made, and an invention for quickly determining the quantity, composition and grain size distribution of the non-metallic inclusions existing on the non-smooth surface after solidification.

The method of evaluating the quantity of the discharged non-metallic inclusions as a characterizing feature of the present invention is a method of evaluating cleanliness of a metal which comprises the steps of levitation-melting a metal piece for a predetermined time by a cold crucible levitation-melting apparatus, discharging non-metallic inclusions existing inside the metal piece, accumulating the non-metallic inclusions discharged to the surface, directly analyzing the same surface after levitation-melting and solidification by a fluorescent X-ray analysis method using an energy dispersion type spectroscope, measuring the quantities of elements constituting the non-metallic inclusions, and determining the quantity of the non-metallic inclusions.

The surface of the sample levitation-melted and solidified by the cold crucible levitation-melting apparatus is curved and non-smooth. Further, the non-metallic inclusions discharged to the sample surface exists in the island form and non-uniformly on the sample surface. To quickly and easily analyze the non-metallic inclusions existing under such a state, the present invention uses the energy dispersion type spectroscope for the fluorescent X-ray analyzer, and measures a relatively broad region (several mm$\phi$ and preferably, at least 10 mm$\phi$). The non-metallic inclusions can be analyzed in further detail and more precisely by analyzing the entire surface of the solidified sample. The present invention can display typically the quantity of the non-metallic inclusions of the whole metal by analyzing the non-metallic inclusions on the metal surface.

The method of analyzing the quantity, composition and grain size distribution of the discharged non-metallic inclusions as another characterizing feature of the present invention is a method of evaluating cleanliness of a metal which comprises the steps of levitation-melting a metal piece for a predetermined time by a cold crucible levitation-melting apparatus, discharging non-metallic inclusions existing inside the metal piece to the surface of a molten body, accumulating the non-metallic inclusions discharged to the surface, then electrolyzing the surface of the sample after levitation-melting and solidification in an acid solution or a halogen/alcohol solution (e.g. bromomethanol solution), or an aqueous type solution (e.g. 10% ferric chloride solution, sodium citrate solution), or a non-aqueous type solution (e.g. acetylacetone solution), extracting and filtrating the non-metallic inclusions, and weighing and analyzing, or weighing and analyzing after separation according to the grain size, the non-metallic inclusions so filtrated.

Further, the present invention carries out a cold crucible treatment by changing $t/\sqrt{(30\ d)}$ (t: retention time for levitation-melting (second), d: maximum inner diameter of the crucible (mm)), examines the diameter L of the non-metallic inclusions occurring at the maximum frequency in each $t/\sqrt{(30\ d)}$, and determines in advance the relation between $t/\sqrt{(30\ d)}$ and L (diameter of impurity particles). Next, when cleanliness of another metal is evaluated, a desired value is selected for $t/\sqrt{(30\ d)}$, and the cold crucible treatment of the other metal is carried out. The occurrence quantity of N of non-metallic inclusions having the diameter L in the other metal is measured by assuming that the diameter L of the non-metallic inclusions occurring at the maximum frequency in the other metal in this selected $t/\sqrt{(30\ d)}$ is the same as that of the metal described above, and N is evaluated as cleanliness of the other metal. The present invention provides also an evaluation method of cleanliness of a metal characterized in that the generation quantities $N_1$, $N_2$, . . . of non-metallic inclusions having diameters of $L_1$, $L_2$, . . . greater than L in the other metal are measured, and these $N_1$, $N_2$, . . . values are evaluated as cleanliness of the other metal.

The metal surface after solidification is observed under magnification using a microscope, etc., and the number of non-metallic inclusions having statistical meaning, that is, at least 10 and preferably at least 40, of the non-metallic inclusions, are selected from those having the maximum diameter, and are plotted on an extreme value statistical chart. The particles having the maximum particle size are then estimated. This extreme value statistical chart is described in detail, for example, in Gumbel "Statistics of Extremes" (published by Seisan-Gijutsu Center Shinsha, Jun. 15, 1978). The outline of this means is as follows in the case of the method of the present invention. A metal is melted, and non-metallic inclusions extracted are then magnified and photographed by a microscope. At least 10, and preferably at least 40, non-metallic inclusions inside the visual field are measured. The number of non-metallic inclusions so measured are re-arranged serially from the smaller size and a cumulative distribution function value is calculated and are plotted on the extreme value probability chart. Next, a recursive formula is calculated, and the maximum non-metallic inclusions are estimated. According to the method of the present invention, cleanness of a metal can be evaluated economically, quickly and with high representativity.

The crucible has the afore-mentioned shape. For example, it is a known crucible ("Material Processing Utilizing Electromagnetic Force". Nos. 129 and 130th Nishiyama Memorial Technical Lectures, published by Iron & Steel Institute of Japan, Foundation, Apr. 28, 1989) which is called a "batch type crucible" or a "levitation-melting type crucible", whose upper surface is opened and whose lower surface is closed.

Figure 5:
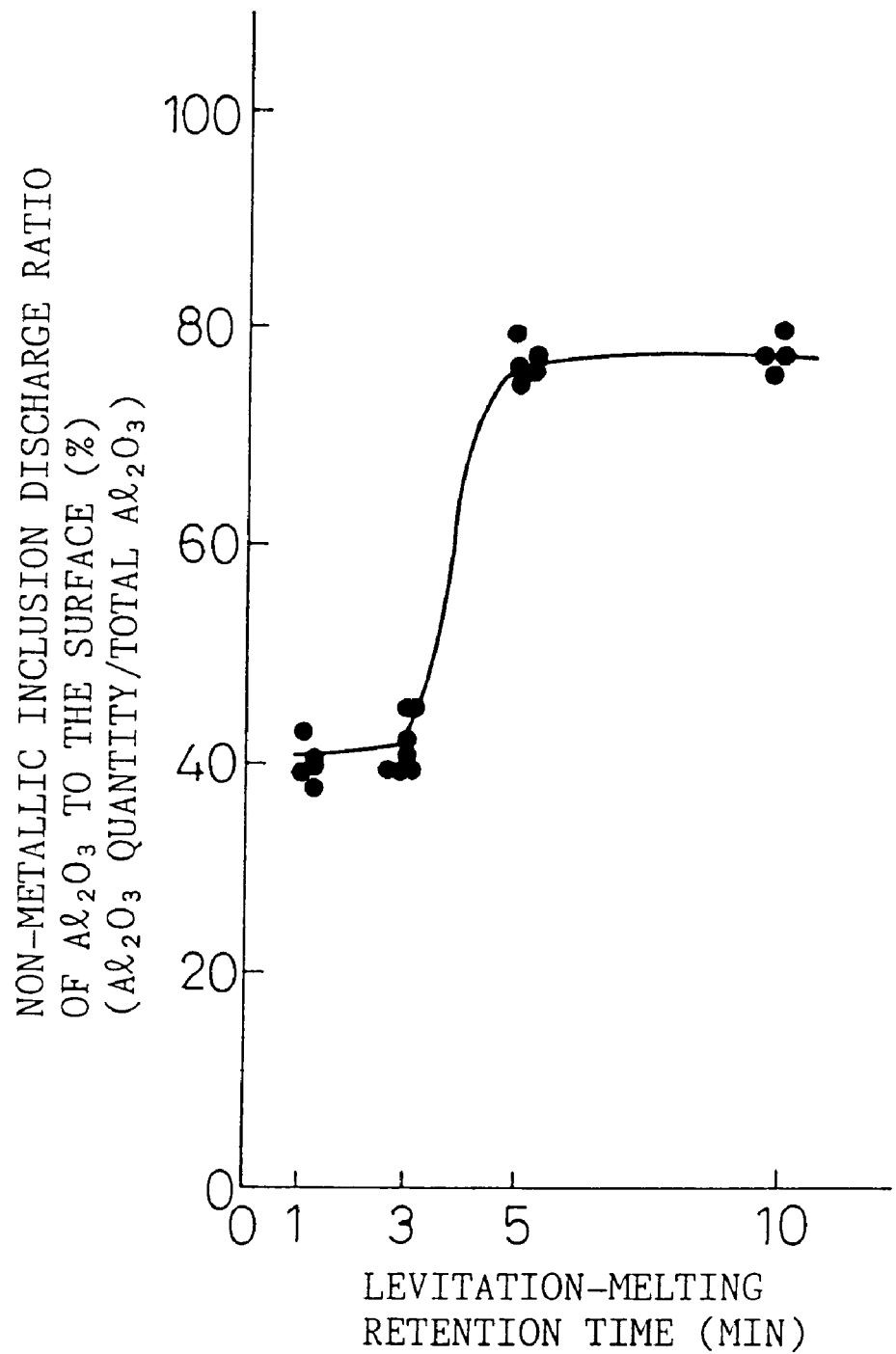
FIG. 5 shows the relation between a levitation-melting retention time and a non-metallic inclusion discharge ratio.
Figure 6:
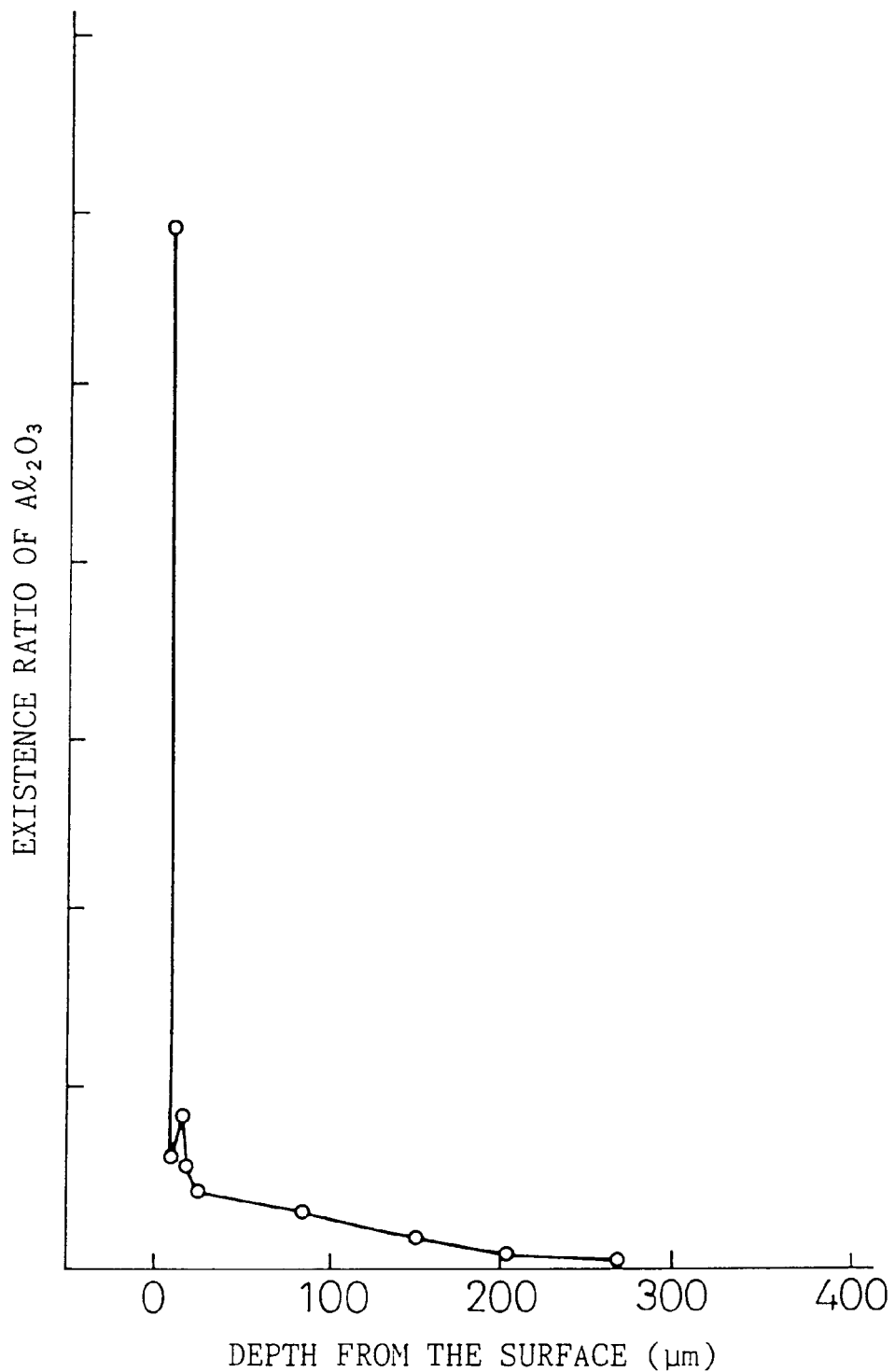
FIG. 6 shows an existence ratio of levitation non-metallic inclusions depending on the surface depth.

FIG. 5 is a diagram showing the relation between an alumina discharge ratio in the sample and a levitation-melting retention time. A sample of a weight of dozens of grams to several kilo-grams is levitation-melted by the cold crucible levitation-melting method, and according to the result of the experiments conducted by the present inventors by using a metal piece of 100 g, it can be seen from FIG. 5 that about 80% of the non-metallic inclusions in the sample are discharged when melting is retained for at least 3 minutes and the discharge ratio does not alter even when the melting retention time is kept longer than 3 minutes. The result of the experiments conducted by the present inventors reveals that almost all the non-metallic inclusions and impurities that are discharged to the surface exist within the depth of about 30 $\mu$m from the surface layer (see FIG. 6). On the other hand, X-ray transmittance is about 100 $\mu$m for iron and dozens of $\mu$m for alumina as a typical non-metallic inclusion. Therefore, in order to directly measure only the region in which the non-metallic inclusions discharged exist, it is most efficient to apply the fluorescent X-ray analysis as is used in the present invention.

The surface of the sample again solidified after levitation-melting is a curved surface and is a non-smooth surface. Therefore, the sample cannot be measured by a wavelength dispersion type fluorescent X-ray method which is generally employed for elementary analysis. For this reason, the present invention uses the energy dispersion type fluorescent X-ray analysis method capable of measuring the curved and non-smooth surface at the sacrifice of analytical accuracy to some extent.

As described above, the non-metallic inclusions discharged to the sample surface exist in the island form and under an extremely heterogeneous state. The experiment conducted by the present inventors teaches that in order to analyze the non-metallic inclusions under such a state, it is necessary to measure at once the regions of several millimeters or to measure several small regions. As a matter of fact, the measurement result having a high level of accuracy can be obtained when measurement is conducted by setting the primary X-ray beams to at least 10 mm. If possible, it is desired to irradiate the primary X-rays to the whole surface of the sample.

On the other hand, most of the fluorescent X-ray analyzers commercially available at present employ predominantly the methods which use narrow primary X-ray beams and measure a very small region but very few analyzers employ the method which expand the primary X-ray beams to several millimeters as is used in the present invention.

Because the present invention analyzes the elementary compositions of the non-metallic inclusions, and the impurity particles, alumina, calcia, silica, magnesia, sodium oxides, etcs., contained in them can be quickly identified and determined quantitatively in accordance with the respective compositions.

To quickly convey the non-metallic inclusion sample accumulating on the sample surface to the fluorescent X-ray analyzers, etc., the present invention disposes an electromagnet or a sucking disk as means for taking out the sample from the crucible so as to suck the sample and to convey it to the analyzer disposed in the proximity of the crucible. The apparatus of the invention includes a handling device having position setting means for positioning the accumulating position of the non-metallic inclusions to a position within the irradiation range of the analyzing X-rays.

As described above, the present invention carries out cold crucible levitation-melting, analyzes the non-metallic inclusions discharged to the sample surface by the energy dispersion type fluorescent X-ray analysis method, and can measure the quantity of the elements constituting the non-metallic inclusions to analyze the component or to identify the components.

As described above, further, almost all the non-metallic inclusions discharged to the surface exist within the depth of about 30 $\mu$m from the surface layer. Therefore, the present invention can recover and analyze almost all the object non-metallic inclusions within an extremely short time of several to dozens of minutes, which is by far shorter than the conventional methods, by melting or electrolyzing about 50 to about 100 $\mu$m of the uppermost surface layer of the sample after solidification. It can be appreciated from this fact, too, that the present invention can provide a method of analyzing the non-metallic inclusions which has sufficient speed and convenience to be used as a management index of the steel production operation.

When the recovered non-metallic inclusions are isolated in accordance with the particle size and are then analyzed, not only the component analysis of the non-metallic inclusions but also the measurement of the particle size and the particle size distribution, the component analysis in accordance with the particle size and the composition analysis in accordance with the particle size become possible.

Figure 7A:
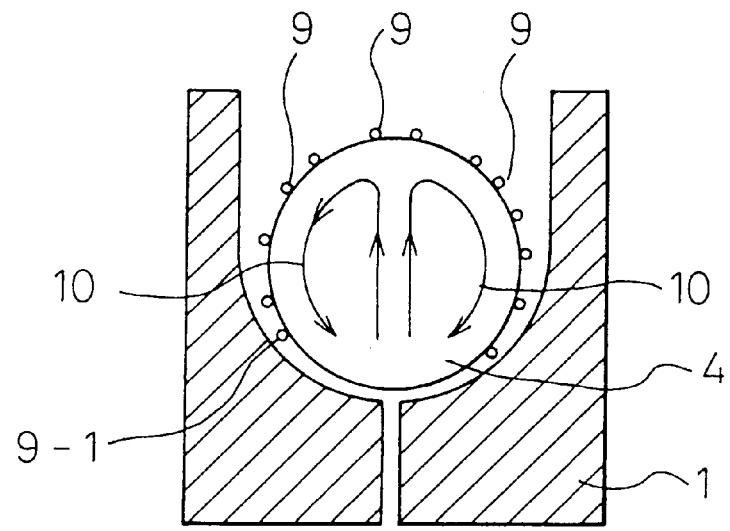
FIG. 7(a) is a view useful for explaining movement of non-metallic inclusions accumulating on the surface of a levitation-melted metal during steady levitation melting.
Figure 7B:
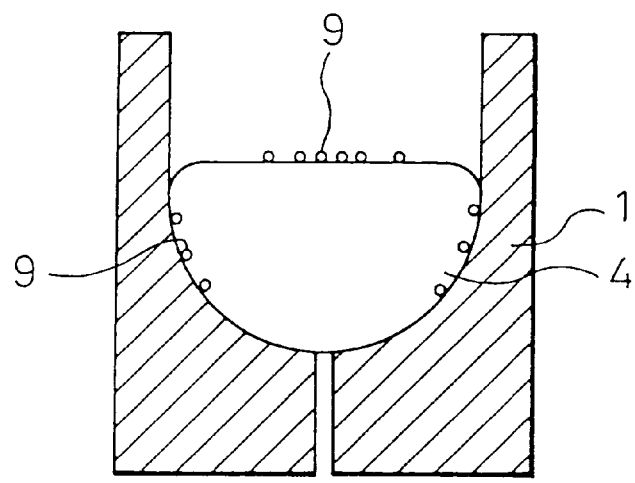
FIG. 7(b) is a view showing the positions of non-metallic inclusions on the surface when the supply of power to a coil is stopped.

FIGS. 7(a) and (b) are schematic views useful for explaining the movement of the non-metallic inclusions discharged to the surface of the levitation-melted metal in the conventional cold crucible method which applies an ordinary single-phase radio frequency current to an induction coil. FIG. 7(a) in an explanatory view when the current is applied and FIG. 7(b) is an explanatory view when the high frequency current is cut off. A gentle stream 10 of the melted metal which rises at the center and flows down along the surface is formed in the levitation-melted metal. A part 9-1 of the non-metallic inclusions discharged to the surface of the molten metal is pushed by this stream 10 of the molten metal and moves to the gap between the levitation-melted metal 4 and the segments 1. When the high frequency current is cut off, the non-metallic inclusions 9-1 do not accumulate on the surface of the top of the molten metal but are pushed to the portion in the proximity of the lower surface of the molten metal as shown in FIG. 7(b). Therefore, when cleanliness of the metal is evaluated in the case of FIG. 7(b), the metal surface of the sample 4 in FIG. 7(b) after solidification is measured. However, because the non-metallic inclusions scatter on the surface and have a broad measurement area, convenience and quickness of the evaluation of non-metallic inclusions are not yet sufficient.

Therefore, in the case of levitation-melting using the single-phase alternating current, the non-metallic inclusions according to the present method spout up around the axis of symmetry of the molten metal and are deposited between the sidewall and the molten metal while being carried by the stream that flows down along the wall of the crucible as shown in FIG. 7(a). When the current to the coil is cut off in this instance, the levitating metal is pushed to the bottom of the crucible due to the gravity as shown in FIG. 7(b), and some of the non-metallic inclusions discharged to the surface are collected by the side portions of the metal while another part moves on the metal. Here, when the current is once held at a level at which the metal under levitating is solidified, and is then cut off after solidification of the metal, the non-metallic inclusions are collected only at the side portion and form a band-like accumulating band.

Figure 8:
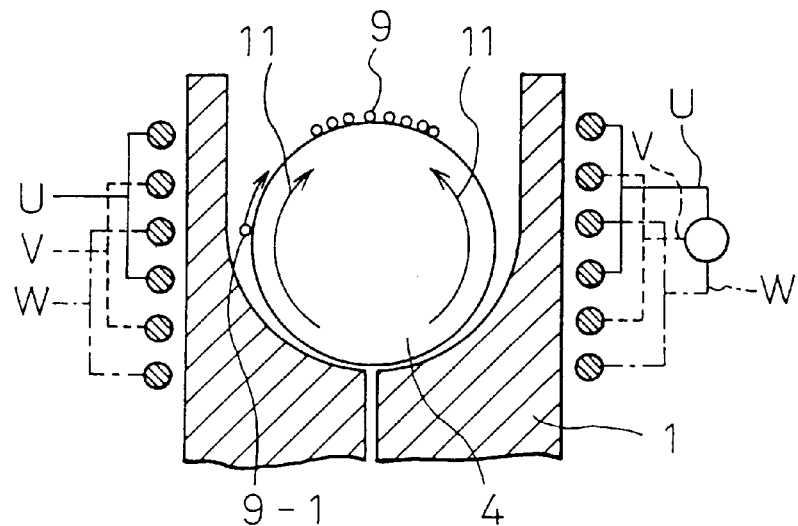
FIG. 8 is a view showing a three-phase A.C. cold crucible apparatus.

FIG. 8 shows an induction heating coil for supplying high frequency currents of U, V and W of the three-phase alternating current having mutually different phases as the induction heating coil of the present invention. This induction heating coil is so constituted as to possess the function of a linear motor for forming an upward stream 11 on the surface of the molten metal 4 which is levitation-melted by the three-phase AC Currents, U, V and W. The high frequency currents U, V and W are so arranged as to allow the metal sample 4 to be levitation-melted. In other words, the induction heating coil according to the present invention levitation-melts the metal sample 4 and forms the upward stream 11 on the surface of the molten metal which is so levitation-melted. When the three-phase alternating current is used in the present invention, the stream becomes upward along the wall of the crucible during melting, too, as shown in FIG. 8. Therefore, the non-metallic inclusions accumulate only at the upper portion, and accumulate at the upper portion, even after solidification, irrespective of the cut-off operation of the current. Consequently, substantially all of the non-metallic inclusions contained in the metal sample can be determined by measuring the non-metallic inclusions of the island-like occupation area at the top of the molten metal, and cleanliness of the metal can be evaluated extremely conveniently and quickly.

EXAMPLES

Example 1

Figure 12:
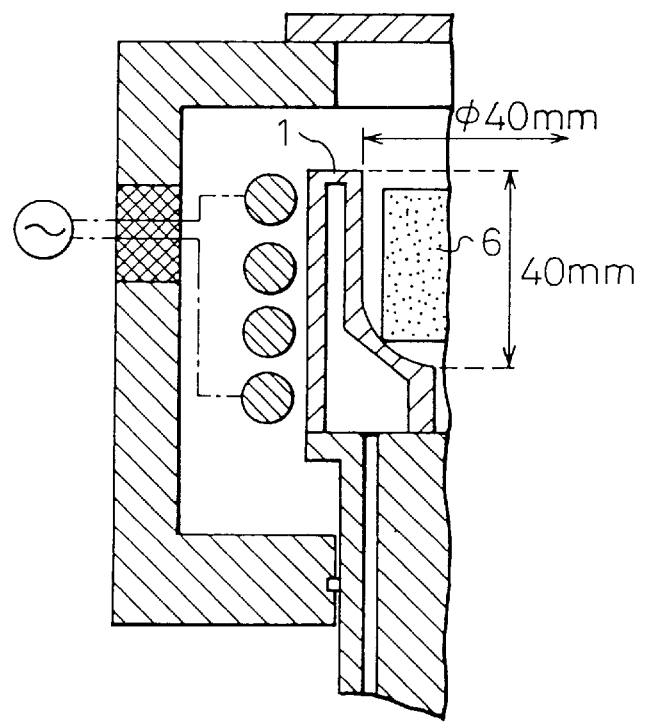
FIG. 12 is a view showing an example of the size of a crucible for levitation-melting used for an embodiment.
Figure 13A:
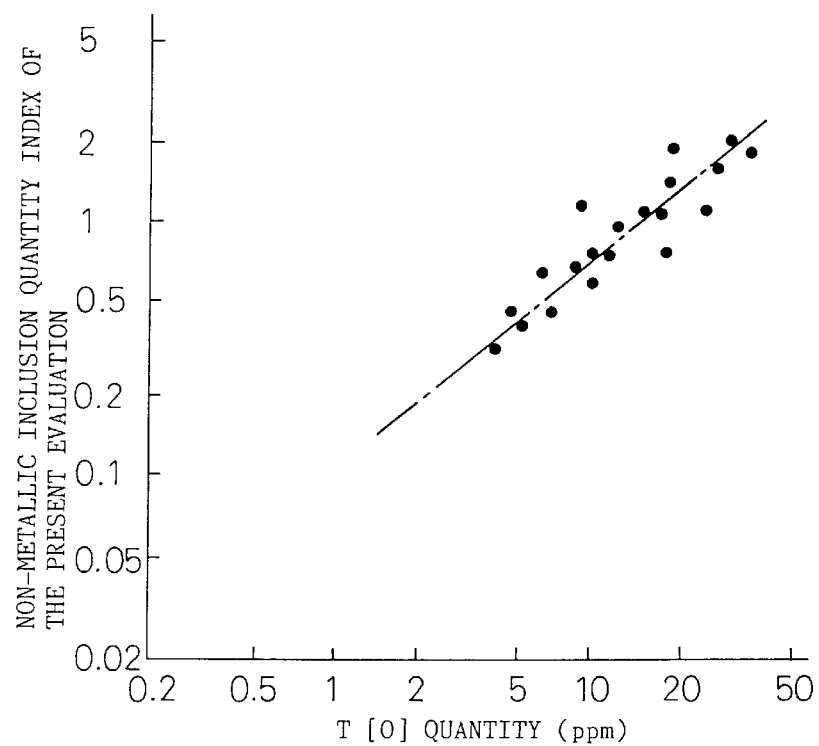
FIG. 13(a) is a diagram showing the correlation between an alumina analysis result and a total oxygen concentration of Example 1.
Figure 13B:
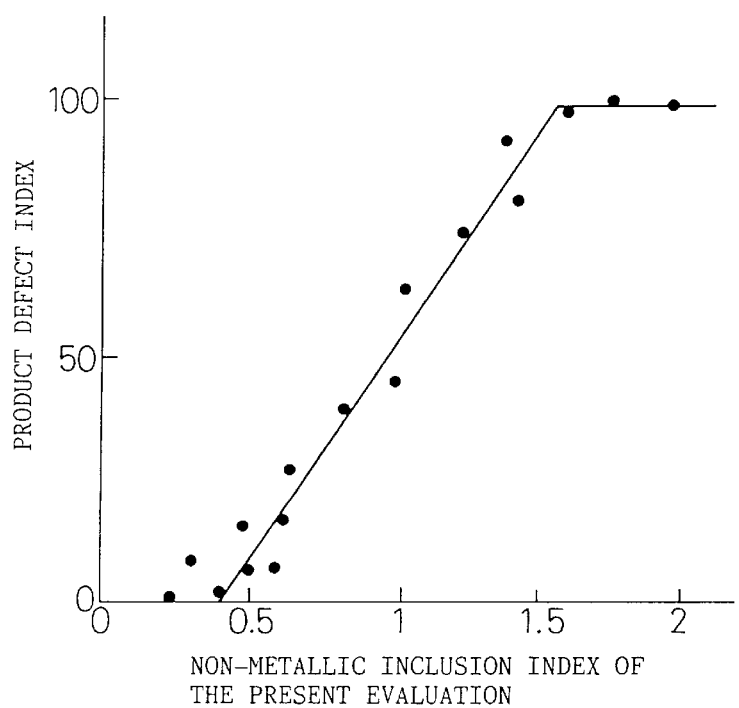
FIG. 13(b) is a diagram showing the relation between product defects and a non-metallic inclusion index.
Figure 13C:
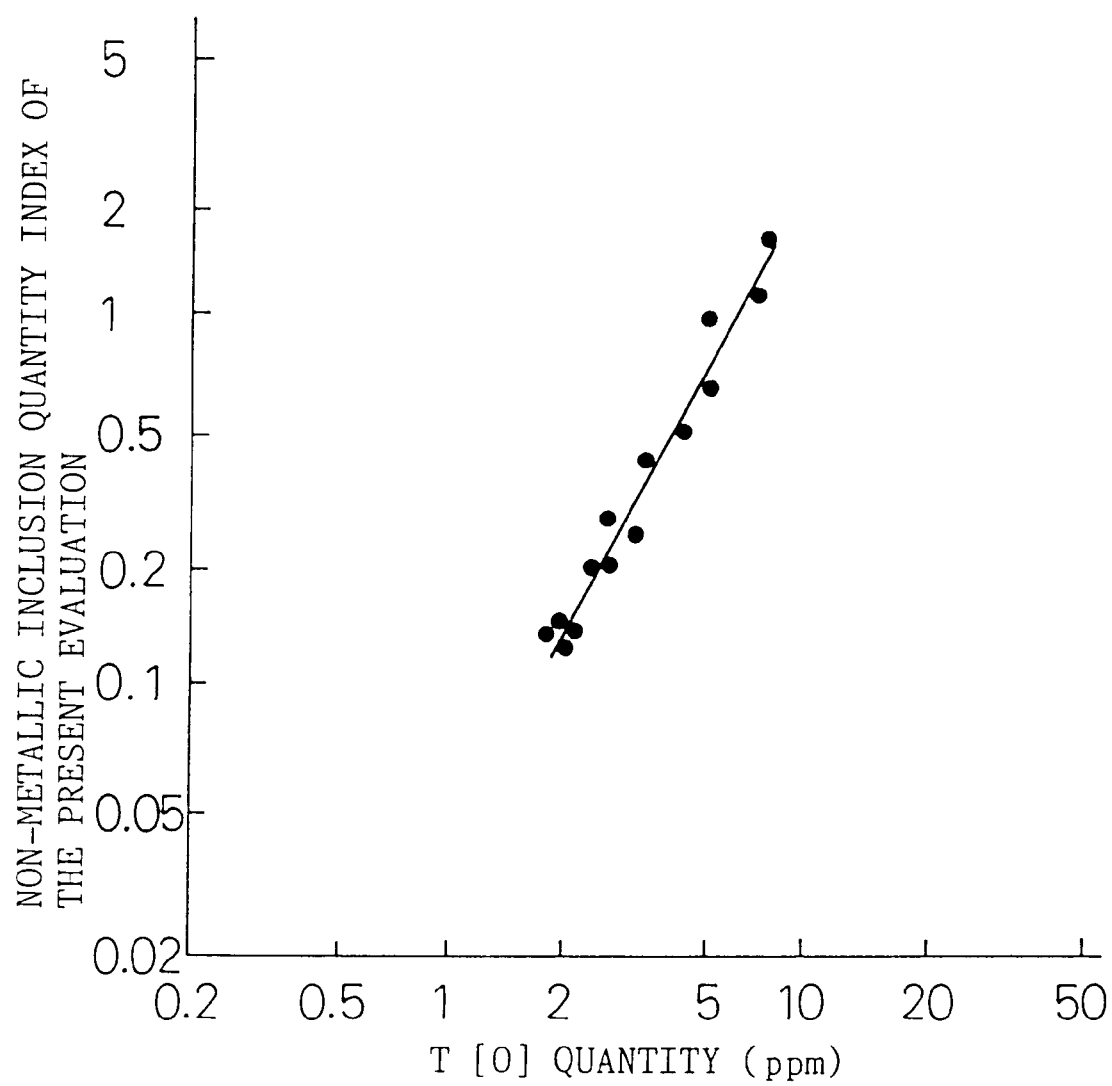
FIG. 13(c) is a diagram showing the correlation between an alumina analysis result and a total oxygen concentration in Example 3.

Twenty cast slabs of low carbon aluminum killed steels were first cast by using a casting mold having a width of 1,500 mm and a thickness of 250 mm at a casting rate of 1.2 m/min. Samples were collected at ¼ and ½ portions from a size of 20 mm in the casting direction, 30 mm from the surface layer in the thickness direction and 20 mm in the transverse direction from these slabs, respectively. Each sample was melted in a crucible having an inner diameter of 40 mm, a depth of 40 mm and a parabolic sectional shape within the range of 20 mm to 40 mm from the upper end shown in FIG. 12 in an atmosphere having a gauge pressure of 0.2 atms with respect to the atmospheric pressure. A power of 30 kW was applied to the coil, and the metal was retained for 5 minutes after melting. Then, power was reduced proportionally to 0 kW in the course of 10 seconds. The molten sample was solidified under the state devoid of the sink and cavity at its top as the final solidification position. Thereafter, the area of the island accumulation of the non-metallic inclusions was examined. Another sample collected from the position very close to the collecting position of each sample and having the same size was subjected to the total oxygen (T[O]) analysis for the purpose of comparison. FIG. 13(*a*) shows the result of their indices and this diagram shows a very close correlationship. Similarly, FIG. 13(*b*) shows the index comparison with a defect index of a product sheet after rolling and surface treatment of the same slab, and a close correlationship could be obtained.

Example 2

Figure 11:
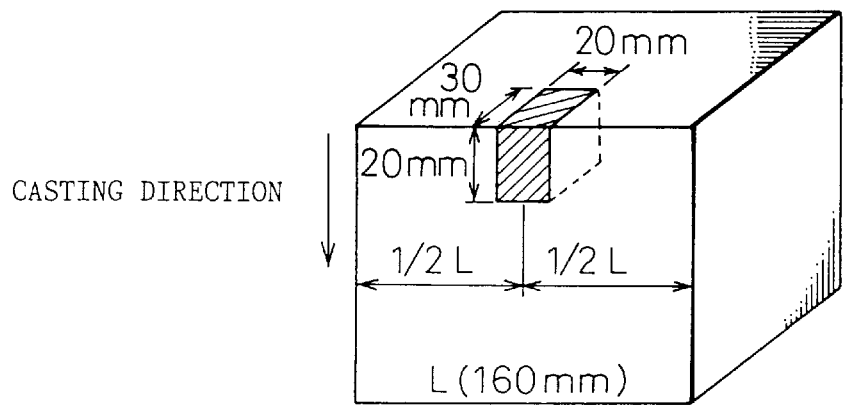
FIG. 11 is a view showing a sample collection position of levitation-melting.

Slabs of a high carbon steel were first cast by a 160 mm-square casting mold at a casting rate of 2 m/min, and each sample was collected at a ½ portion of the side of each slab from a size of 20 mm in the casting direction, 30 mm from the surface layer in the thickness direction and 20 mm in a peripheral direction as shown in FIG. 11. Each sample was melted in a crucible having an inner diameter of 40 mm, a depth of 40 mm and a parabolic sectional shape within the range of 20 mm to 40 mm from the upper end as shown in FIG. 12 in an atmosphere having a gauge pressure of 0.2 atm with respect to the atmospheric pressure. A power of 30 kW was applied to the coil, and the molten metal was retained for 5 minutes after melting. Power was thereafter reduced. The molten sample was solidified under the state devoid of sink and cavity at the top thereof as the final solidification position. Thereafter, the non-metallic inclusions electrolytically extracted from the surface of the sample molten and solidified were gathered on a filter, and were observed through a microscope. Statistical calculation of extremes of the maximum non-metallic inclusions was carried out for each field from 50 fields (one field: 0.02833 mm$^2$), and the non-metallic inclusions having the maximum particle diameter were estimated. On the other hand, 50 samples having the same size were melted, the non-metallic inclusions having the maximum particle diameter on each sample surface were examined, and they were compared with the estimation result. Table 2 shows the estimated particle diameters by the statistical extremes and the particle diameters of the maximum non-metallic inclusions on the surface of the fifty samples. A result substantially coincide with the estimated particle diameters could be obtained.

TABLE 2

| | statistical extremes estimation | experiment evaluation value |
|---|---|---|
| diameter of maximum inclusions | 15 μm | 16 μm |

Example 3

Twenty cast slabs of a low carbon aluminum killed steel were first cast by using a casting mold having a width of 1,500 mm and a thickness of 250 mm at a casting rate of 1.2 m/min, and samples were collected at ¼ and ½ portions in the transverse direction of the slabs from a size of 20 mm in the casing direction, 30 mm from the surface layer in the thickness direction and 20 mm in the transverse direction. Each sample was melted in a crucible having an inner diameter of 40 mm, a depth of 40 mm and a parabolic sectional shape within the range of 20 mm to 40 mm from the upper end as shown in FIG. 12 in an Ar atmosphere at atmospheric pressure. The sample was held for 5 minutes after melting, and was solidified after discharging the non-metallic inclusions.

Figure 14:
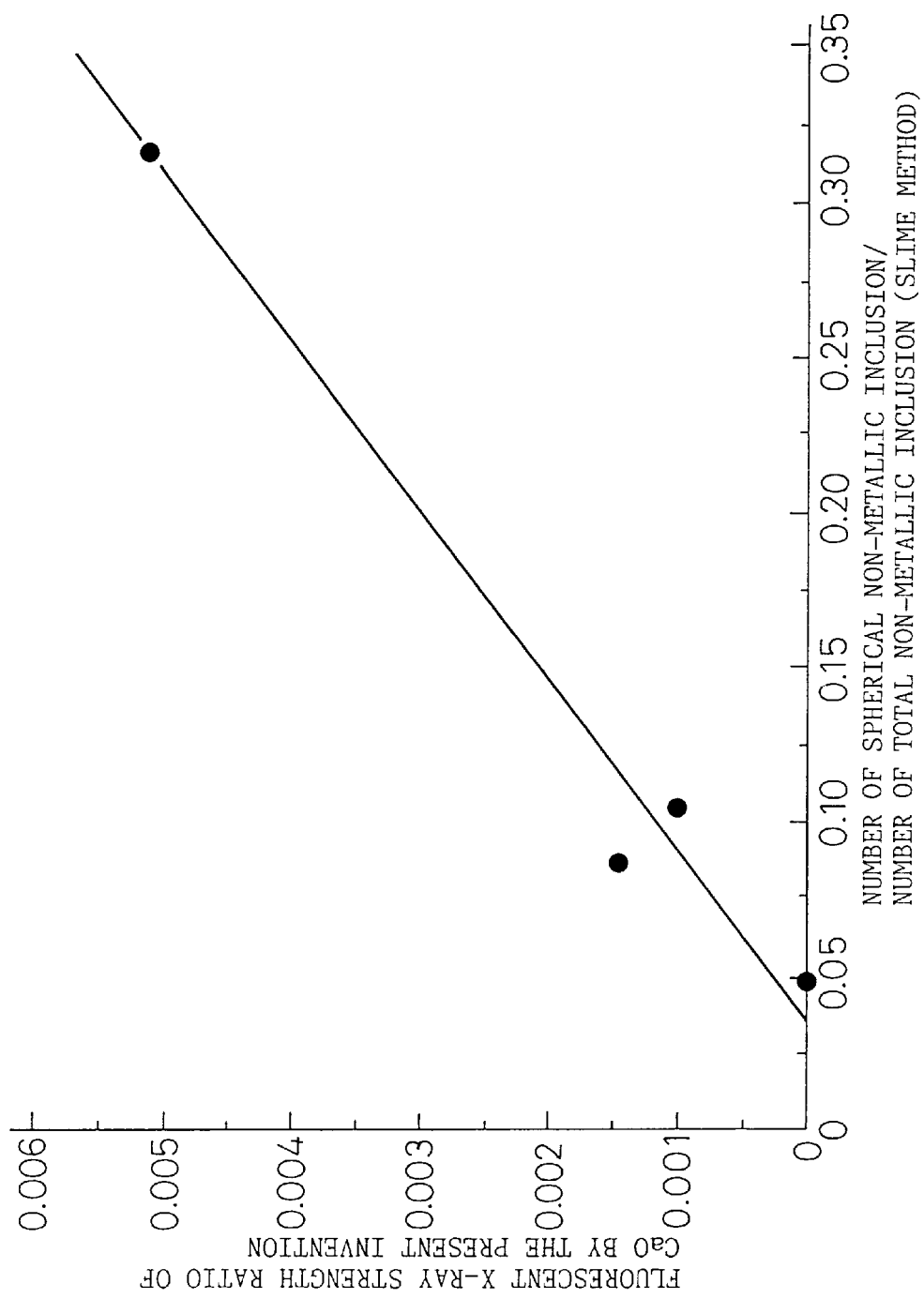
FIG. 14 is a diagram showing the correlation between a CaO analysis result and an analysis result by a slime method.
Figure 15:
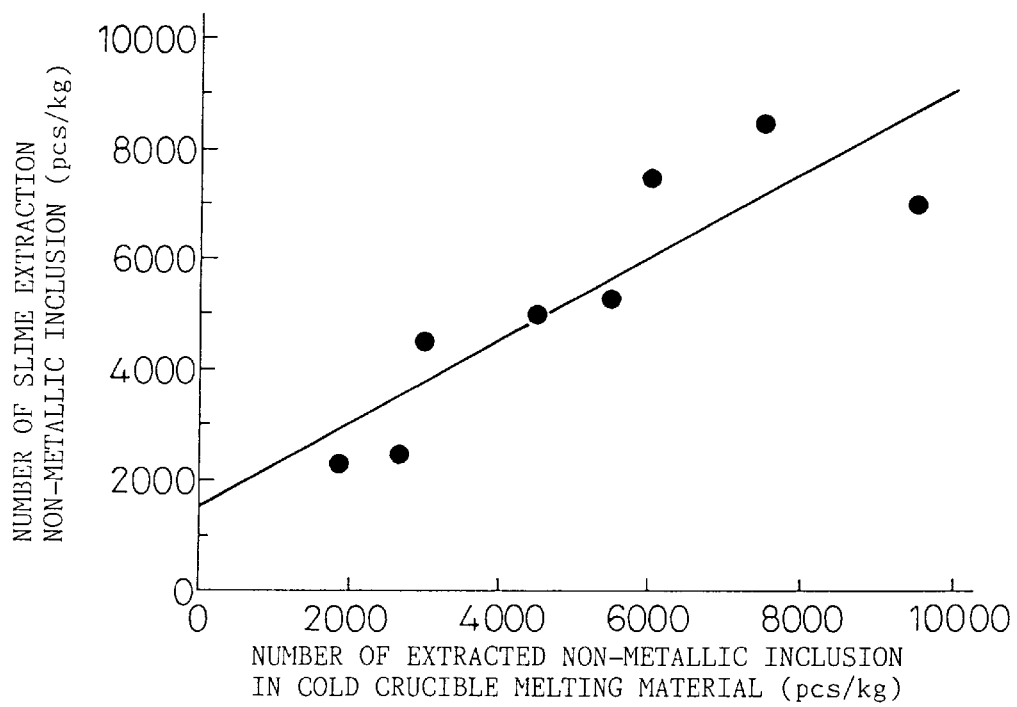
FIG. 15 is a diagram showing the relation between the number of extracted non-metallic inclusions of a cold crucible melted material and the number of extracted inclusions of a slime method according to the prior art.
Figure 16:
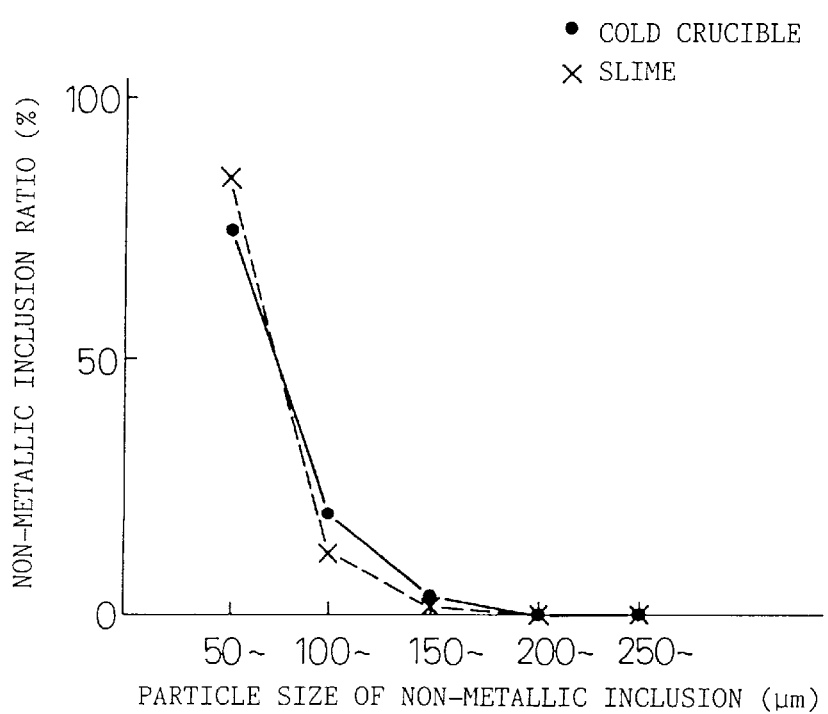
FIG. 16 is a diagram showing the relation of a grain size of non-metallic inclusions and the proportion of the number of non-metallic inclusions.

The non-metallic inclusions accumulating in an island form on the surface of the sample after re-solidification were analyzed by fluorescent X-ray analysis. Measurement was carried out at an intensity of primary X-rays of 1 μA×50 kV, an irradiation diameter of 13 mm and an irradiation time of 30 seconds. The quantity of alumina, silica, calcia, etc., in the sample was measured from the fluorescent X-ray intensity of At, Si, Ca, etc. At the same time, each sample collected from the position closest to the same sample and having the same size was subjected to the total oxygen analysis. When both measurement results were compared, the aluminum intensity obtained by the fluorescent X-ray analysis and the total oxygen exhibited a close correlation as shown in FIG. 13(*c*). When calcium in the non-metallic inclusions of a similar sample collected separately was analyzed by the X-ray analysis in accordance with the method of the present invention and was compared with CaO obtained by the slime method to determine the correlationship with CaO, they exhibited a close correlation as shown in FIG. 14. It can be seen from FIG. 16 that the result hardly changes from the result of the slime method in the case of the size distribution of a 50 μm interval. FIG. 15 shows the result obtained by measuring the quantity of the non-metallic inclusions contained in the sample inside a tundish by the method of the present invention and comparing it with the slime method. As can be seen from the diagram, the quantity of the non-metallic inclusions was great inside the tundish but was small in the slab. In this way, the inclusions inside the steel sample could be evaluated economically, quickly and conveniently.

In other words, the method of the present invention can evaluate the non-metallic inclusions within a time of about 5 minutes for cold crucible levitation-melting, about 1 minute for the fluorescent X-ray analysis and a few minutes for fitting the sample to the apparatus, or within about 10 minutes in total, and can evaluate quality of the slab within a far shorter time than the conventional evaluation method.

Example 4

Twenty slabs of a low carbon aluminum killed steel were first cast by using a casting mold having a width of 1,500 mm and a thickness of 250 mm at a casting rate of 1.2 m/min, and each sample was collected at ¼ and ½ portions in the transverse direction of the slabs from a size of 20 mm in the casting direction, 30 mm from the surface layer in the thickness direction and 20 mm in the transverse direction. Each sample was melted in a crucible having an inner diameter of 40 mm, a depth of 40 mm and a parabolic sectional shape within the range of 20 mm to 40 mm from the upper end as shown in FIG. 12 in an Ar atmosphere at atmospheric pressure. The sample was held for 5 minutes after melting, and after the non-metallic inclusions were discharged, the sample was solidified.

The surface of each sample after re-solidification was analyzed by the surface electrolysis method of the present invention. For example, the steel as the matrix was electrolyzed in a weight of about 0.5 g by setting the sample to be melted into a 10% acetylacetone type electrolyte as an anode under the current density of 5 to 50 mA/cm$^2$. The non-metallic inclusions discharged on the sample surface were left in the solution as the residue of electrolysis. After the electrolysis was completed, the non-metallic inclusions were collected as the residue on the filter. Weighing and separation in accordance with the particle size or component analysis were carried out for this residue.

As the method of analyzing the non-metallic inclusions, the residue on the filter was analyzed by the fluorescent X-ray analysis. Alternatively, after the filter containing the residue was heated and ashed in a platinum crucible, it was fused by a fusing agent comprising the mixture of sodium carbonate, potassium carbonate and sodium borate, and after the fused product was heated and dissolved by using a dilute hydrochloric acid solution, it was analyzed by plasma emission spectroscopic analysis or atomic absorption analysis.

An ultrasonic sieving method was employed as a method of measuring the particle size of oxides. The residue on the filter was dispersed in a methanol solution or an ethanol solution by using an ultrasonic wave. This solution was poured onto a filter having a suitable mesh and was filtrated and classified by applying ultrasonic vibration. The particle size distribution and the component composition of the non-metallic inclusions were determined by the weight of the residues and their chemical analysis values on the respective filters.

Figure 10:
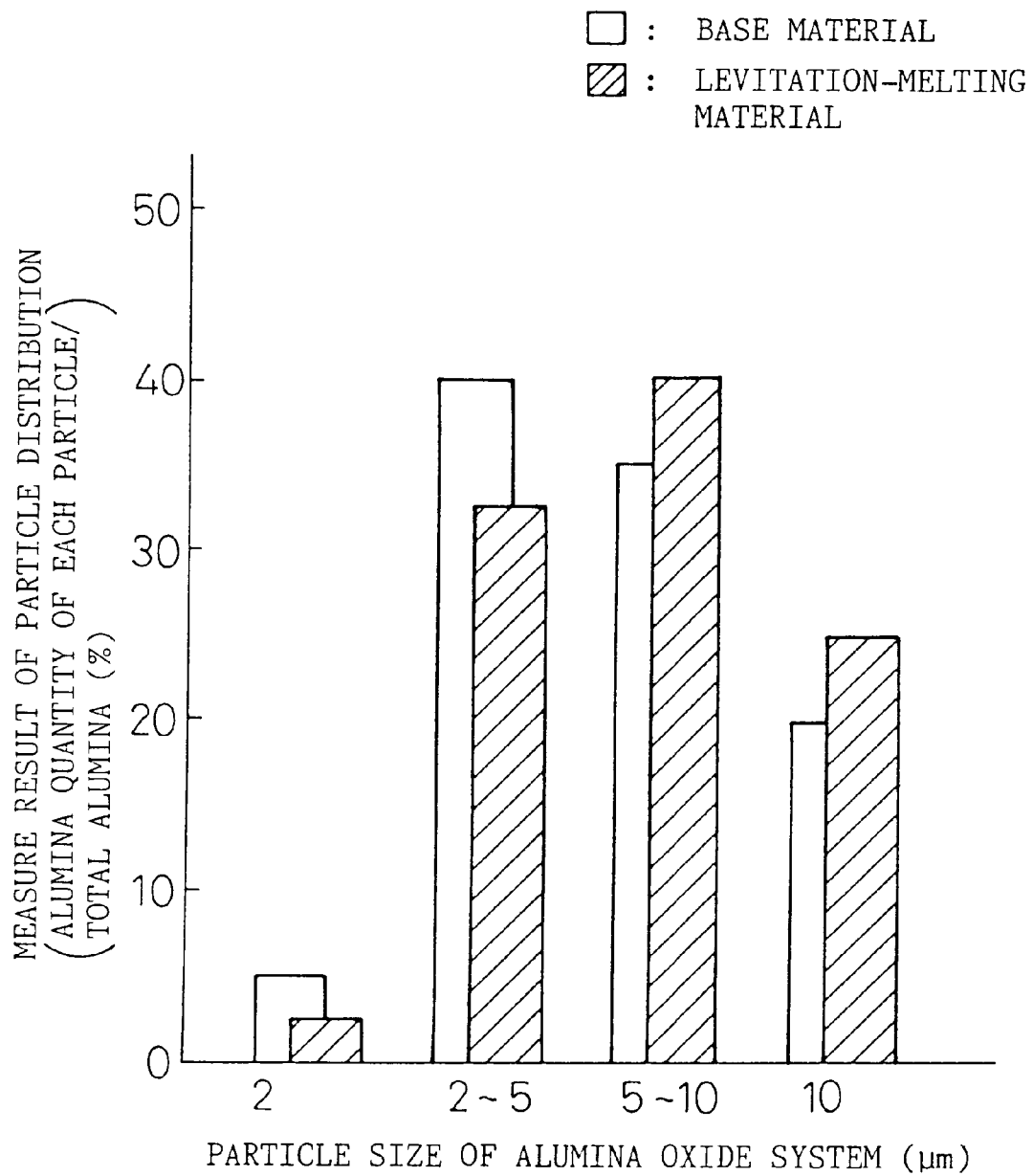
FIG. 10 is a diagram showing non-metallic inclusion distributions of a base metal and a levitation-melted material by a surface electrolytic method.

As shown in FIG. 10, it was found out that the oxides which were concentrated on the surface by levitation-melting and were electrolytically extracted had substantially the same extraction frequency in accordance with each particle diameter as that of the oxides extracted directly from the base metal by electrolysis which was the same as the sample used for levitation-melting. In other words, according to the evaluation method of the present invention, the information of the non-metallic inclusions of the base metal itself could be obtained without modification of the inclusions, etc., during the test. Therefore, the evaluation method of the present invention could drastically shorten the time necessary in the past for evaluating the quality of slabs.

Figure 17:
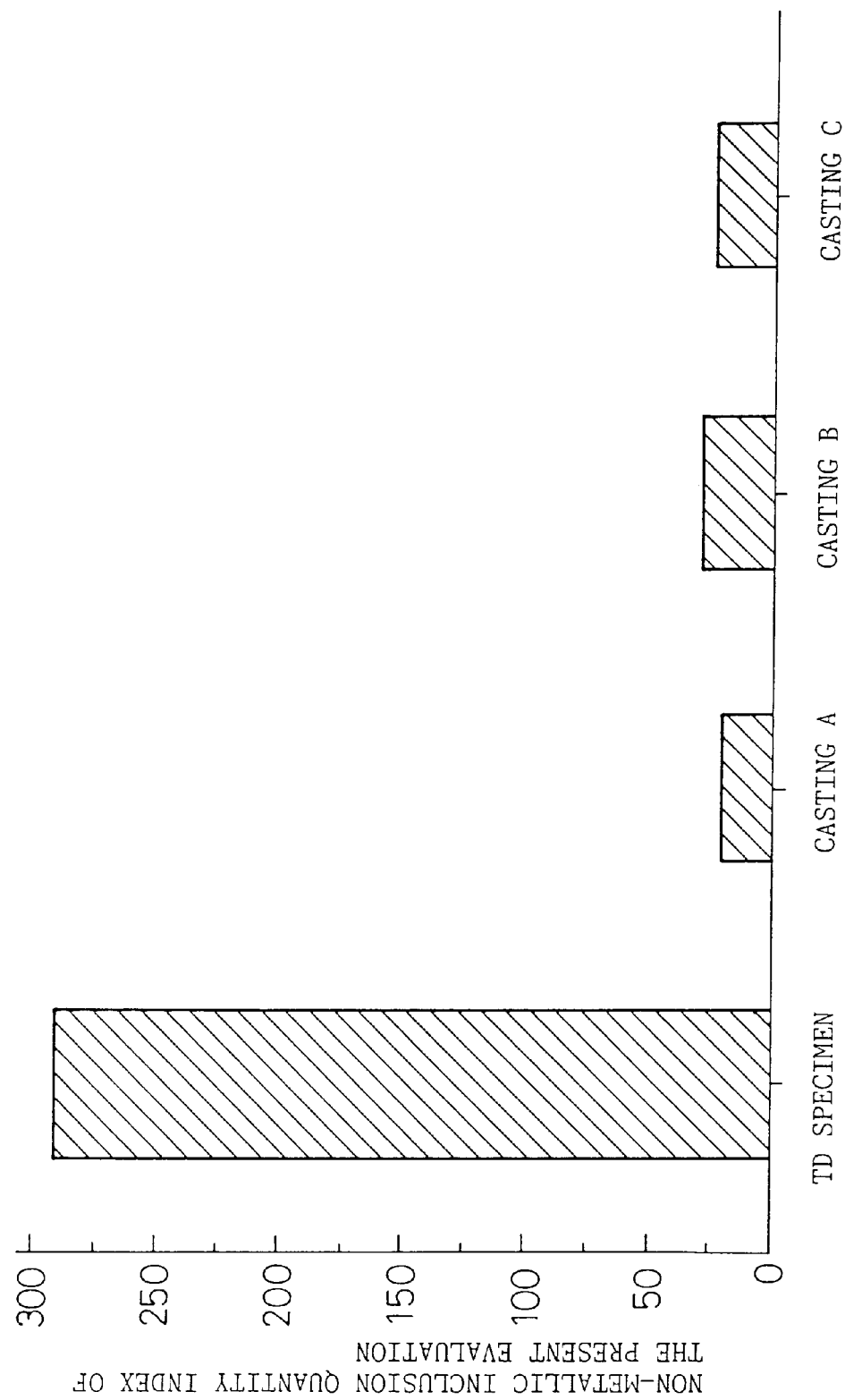
FIG. 17 is a diagram showing an evaluation example of non-metallic inclusions in an iron sample.

FIG. 17 shows the results of the non-metallic inclusions contained in the sample inside the tundish and the non-metallic inclusions contained in the sample, and their comparison result. As can be appreciated from the diagram, the evaluation method of the present invention could evaluate economically, quickly and conveniently the non-metallic inclusions in the steel samples to find out, for example, that the quantity of the non-metallic inclusions was great in the tundish and was small in the slabs.

Example 5

The inventors of the present invention collected samples from a portion about 30 mm below the skin of continuous cast slabs of a low carbon aluminum killed steel having a thickness of 250 mm, and levitation-melted the samples by using a cold crucible having a maximum inner diameter of 30 mm in an Ar atmosphere at atmospheric pressure. The levitation-melted metal was then held for t seconds described later, and was then solidified. Particles of non-metallic inclusions accumulating on the surface of the solidified body could be observed by eye. The solidified body having the non-metallic inclusion particles accumulating on the surface thereof was set as an anode to a 10% acetylacetone type electrolyte solution, and was electrolyzed to a weight of 0.5 g with the impurity particles on the surface of the solidified body at a current density of 5 to 50 mA/cm$^2$. Thereafter, the electrolyte solution was filtrated, and the residue on the filter was dispersed by the ultrasonic sieving method and was then poured onto a metallic filter having meshes of desired sizes to as to conduct filtration and classification by applying ultrasonic vibration.

The present inventors conducted the experiment described above three times for a continuous cast slab of the same charge, that is, the case where the retention time was 60 seconds, 120 seconds and 180 seconds. The non-metallic inclusion particles were classified into the following eight kinds in accordance with their sizes, that is, the first kind (exceeding 300 μm), the second kind (250 to 300 μm), the third kind (200 to less than 250 μm), the fourth kind (150 to less than 200 μm), the fifth kind (100 to less than 150 μm), the sixth kind (50 to less than 100 μm), the seventh kind (10 to less than 50 μm) and the eighth kind (less than 10 μm).

Figure 18:
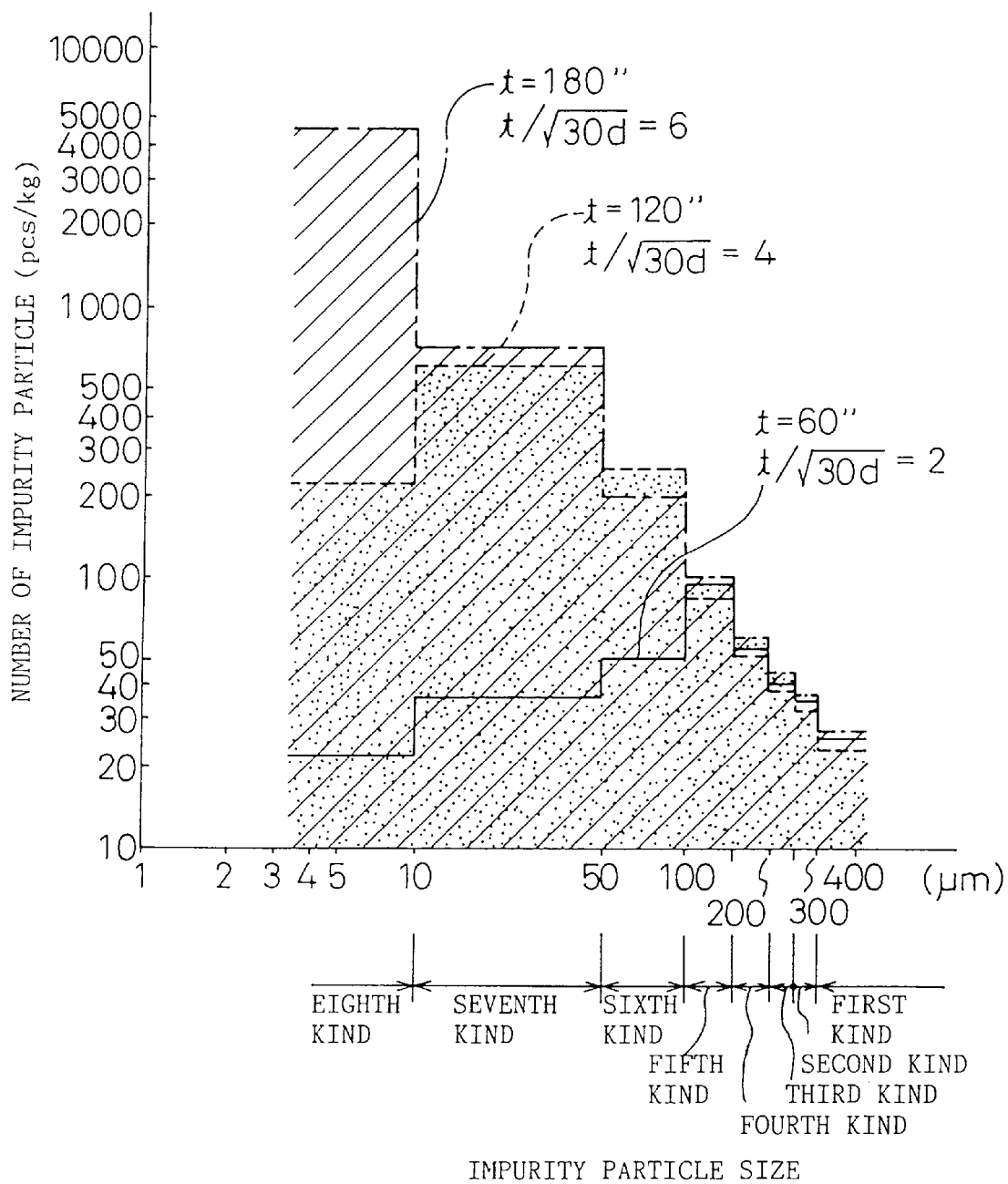
FIG. 18 is a diagram showing the occurrence state of non-metallic inclusion particles by a cold crucible having a maximum inner crucible diameter of 30 mm.

FIG. 18 shows the result of the experiment, and the ordinate represents the number of the non-metallic inclusions per kg metal piece. As can be seen from the histogram of t=60" (solid line), the sizes of the non-metallic inclusion particles occurring at the maximum frequency were of five kinds and ranged from 100 to 150 μm when the retention time t of the levitation-molten metal was 60 seconds. As can be seen from the histogram of t=120" (dotted line), on the other hand, the non-metallic inclusion particles were of seven kinds. As can be seen from the line graph of t=180" (one-dot-chain line), the non-metallic inclusion particles at the maximum frequency were of eight kinds when the retention time of the levitation-molten metal was 180 seconds.

As can be seen from FIG. 18, large non-metallic inclusion particles of the first to fifth kinds mostly accumulated on the surface of the molten metal at the retention time of 60 seconds, and their number hardly increased when the retention time was extended to 120 seconds or 180 seconds. The non-metallic inclusion particles of the medium sizes of the sixth and seventh kinds did not sufficiently accumulate on the surface of the molten metal at the retention time of 60 seconds, but all of them gathered on the surface of the molten metal at the retention time of 120 seconds. Further, their number hardly increased even when the retention time was extended to 180 seconds. The small non-metallic inclusion particles of the eighth kind did not gather sufficiently at the retention time of 120 seconds, but almost all of them gathered on the surface of the molten metal when the retention time was 180 seconds.

The present inventors collected the samples from the portions about 30 mm beneath the skin of the same continuous cast slabs as those shown in FIG. 18 by using a cold crucible having a maximum inner diameter of 100 mm in place of the crucible having the maximum inner diameter of 30 mm in FIG. 18, and conducted experiments in the same way. In this case, the retention time t of the levitation-melted metal was 55 seconds, 110 seconds, 220 seconds and 330 seconds. The non-metallic inclusion particles gathered on the surface of the levitation-melted metal were processed and classified in the same way as in FIG. 18.

Figure 19:
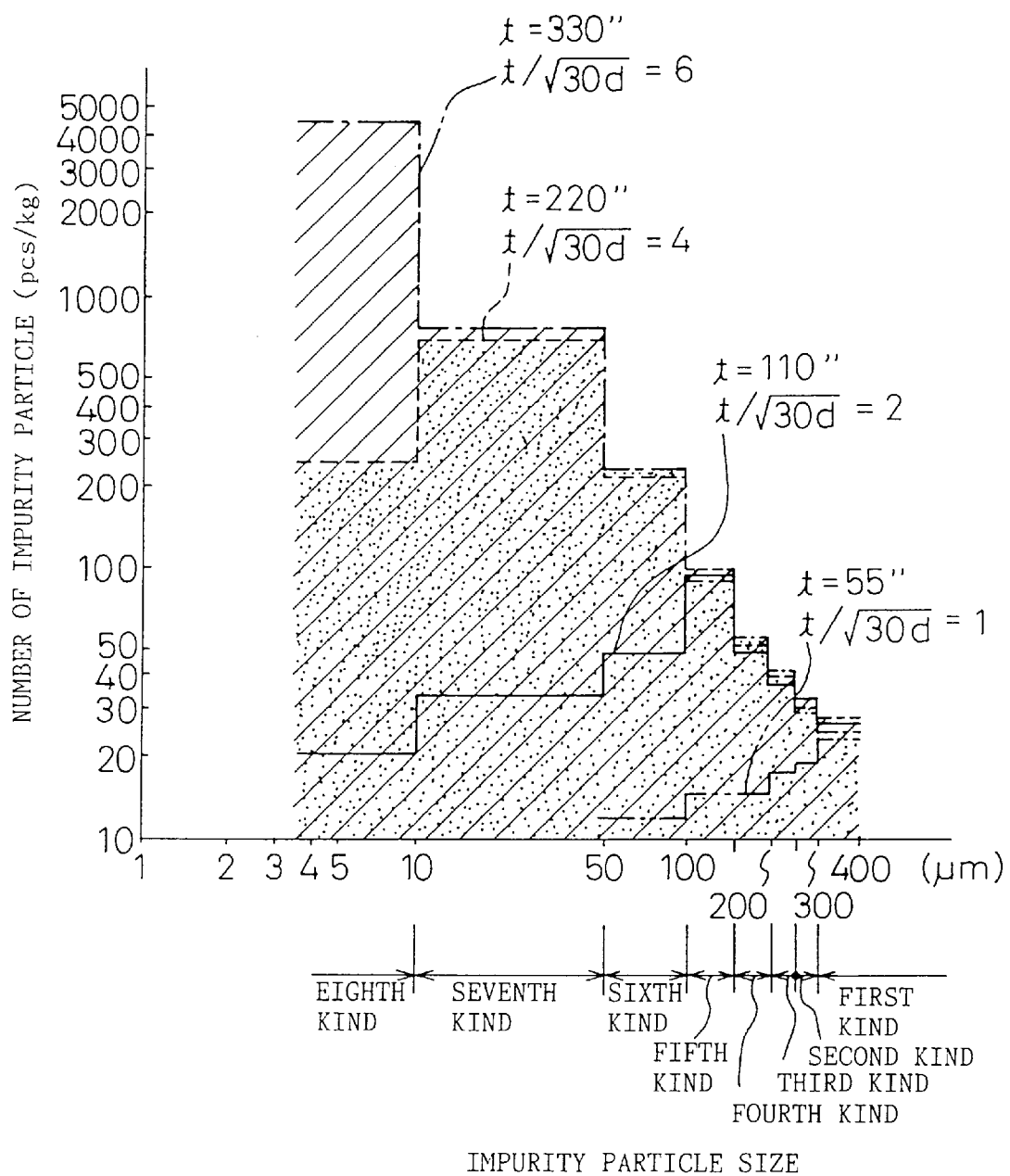
FIG. 19 is a diagram showing the occurrent state of non-metallic inclusion particles by a cold crucible having a maximum inner crucible diameter of 100 mm.

FIG. 19 shows the results of the experiments. As can be seen from the line graph of two-dot-chain lines representing the case of t=55", extremely large non-metallic inclusion particles of at least one kind gathered when the retention time of the levitation-melted metal was 55 seconds, but the accumulation of smaller non-metallic inclusion particles was not sufficient. The retention time t at which the five kinds of non-metallic inclusion particles having the sizes of 100 to 150 μm attained the maximum frequency was 60" in FIG. 18 but was 110" in FIG. 19. Similarly, the retention time at which the seven kinds of the non-metallic inclusion particles having the sizes of 10 to 50 μm attained the maximum frequency was 120" in FIG. 18, but was 220" in FIG. 19.

As described above, when the cold crucible having the different maximum inner diameter was used, it was not possible to accumulate the non-metallic inclusion particles having the same size unless the retention time t of the levitation-melted metal was changed. Even when the inner diameter d of the crucible was changed, however, it was possible to gather the non-metallic inclusion particles having the same size if the ratio $t/\sqrt{(30\ d)}$ of the maximum inner diameter of the crucible to the retention time t of the levitation-melted metal remained the same as shown in FIGS. 18 and 19 when this ratio $t/\sqrt{(30\ d)}$ was used. In other words, when the ratio $t/\sqrt{(30\ d)}$ was 2, five kinds attained the maximum frequency in both FIGS. 18 and 19 and when $t/\sqrt{(30\ d)}$ was 4, seven kinds attained the maximum frequency in both FIGS. 18 and 19.

Therefore, in the present invention, when a crucible having a different size was used, the retention time of the levitation-melted metal was adjusted by using $t/\sqrt{(30\ d)}$. This adjustment made it possible to correctly grasp the non-metallic inclusion particles even when a crucible having different size was used, and made it also possible to directly compare the results of the measurements of the non-metallic inclusion particles carried out by using crucibles having mutually different sizes.

According to an observation made by the inventors of the present invention, macroscopic non-metallic inclusion particles exceeding 300 μm observed in the cold crucible method were not desirable for all kinds of steel materials, and it was always desired to determine them. As can be seen from the line graph of the two-dot-chain line in FIG. 19, these macroscopic non-metallic inclusion particles almost all accumulated when $t/\sqrt{(30\ d)}=1$. Therefore, $t/\sqrt{(30\ d)}$ in the present invention was set to at least 1.

Though not shown in FIGS. 18 and 19, the observation of the present inventors revealed that when $t/\sqrt{(30\ d)}$ was at least 6, the quantity of very small non-metallic inclusion particles slightly increased. However, this slight increase of the very small non-metallic inclusion particles saturated at $t/\sqrt{(30\ d)}$ of 20. Therefore, the ratio $t/\sqrt{(30\ d)}$ exceeding 20 was not necessary, and $t/\sqrt{(30\ d)}$ in the present invention was limited to not greater than 20.

The present invention collected the samples from continuous cast slabs different from those of FIG. 18 and conducted the experiments by using a cold crucible having a maximum inner diameter of 30 mm by changing the retention time of the levitation-melted metal to 60 seconds, 120 seconds and 180 seconds. The impurity particles gathered on the surface of the levitation-melted metal were processed and classified in the same way as in FIG. 18.

Figure 20:
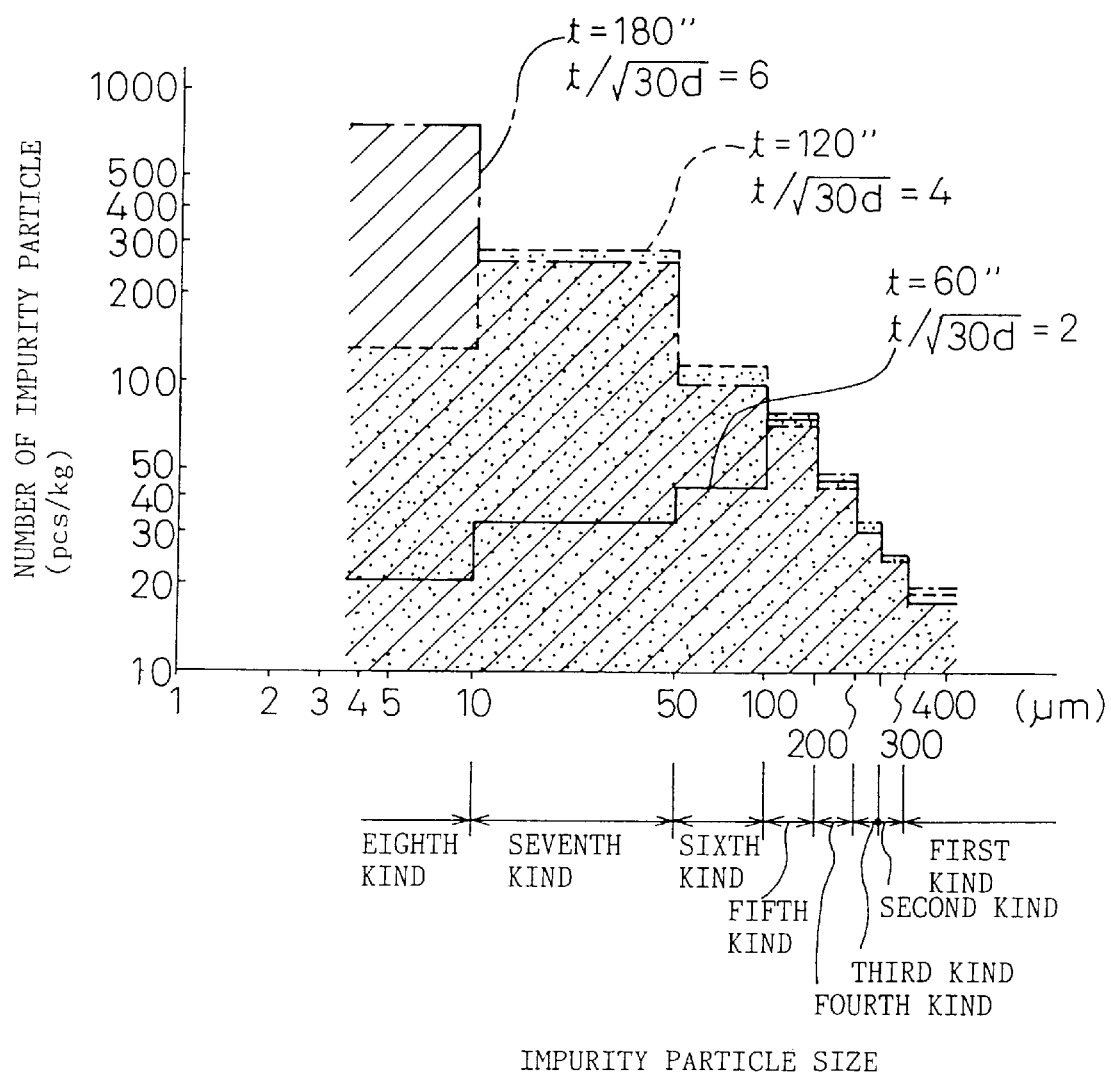
FIG. 20 is a diagram showing the occurrence state of non-metallic inclusion particles in a continuous casting slab different from that of FIG. 18.

FIG. 20 shows the results of these experiments. Since the continuous cast slabs having a different charge from those shown in FIG. 18 were used in FIG. 20, the numbers of non-metallic inclusion particles were different from those in FIG. 18. However, the number of kinds of the sizes of the non-metallic inclusion particles occurring at the maximum frequency when $t/\sqrt{(30\ d)}$ was 2 was five kinds in the same way as in FIG. 18, the number of kinds of the non-metallic inclusion particles at the maximum frequency was seven kinds in the same way as in FIG. 18 when $t/\sqrt{(30\ d)}$ was 4, and the number of kinds of the non-metallic inclusion particles at the maximum frequency was eight kinds in the same way as in FIG. 18 when $t/\sqrt{(30\ d)}$ was 6. Large non-metallic inclusion particles of the first to fifth kinds mostly gathered on the surface of the molten metal at $t/\sqrt{(30\ d)}$ of 2 in FIG. 20 in the same way as in FIG. 18, and their number hardly increased even when $t/\sqrt{(30\ d)}$ was increased to 4 or 6. The non-metallic inclusion particles having medium sizes of the sixth to seventh kinds did not sufficiently accumulate on the surface of the molten metal at $t/\sqrt{(30\ d)}$ of 2, but mostly gathered on the surface of the molten metal at $t/\sqrt{(30\ d)}$ of 4 and hardly increased thereafter even when $t/\sqrt{(30\ d)}$ was set to 6.

In other words, even when the charge of the continuous cast slabs to be measured was different, five kinds of non-metallic inclusion particles appeared at the maximum frequency at $t/\sqrt{(30\ d)}$ of 2, and seven kinds of non-metallic inclusion particles appeared at the maximum frequency at $t/\sqrt{(30\ d)}$ of 4. In the present invention, the cold crucible treatments were carried out by changing $t/\sqrt{(30\ d)}$ to 2, 4 and 6 for the continuous cast slabs of the charge shown in FIG. 18, for example, and the result that the diameters L of the non-metallic inclusion particles occurring at the maximum frequency at each $t/\sqrt{(30\ d)}$ were 5, 7 and 8 kinds, was determined in advance.

When the number of kinds of the diameters was determined in advance as described above, it became possible to estimate that the diameters L of the non-metallic inclusion particles occurring at the maximum frequency in the case of FIG. 20 were of seven kinds, by carrying out the cold crucible treatment by selecting the value 4 for $t/\sqrt{(30\ d)}$ when cleanliness of the continuous cast slabs shown in FIG. 20 was evaluated. In this instance, the present invention measured the quantity N pcs/kg of the non-metallic inclusion particles having seven kinds of L. Alternatively, the quantities $N_1, N_2, \ldots, N_7$ of the first to seventh kinds of non-metallic inclusion particles having L of at least 7 were measured.

For example, the continuous cast slabs were subjected to plastic working to obtain steel products. In this instance, the non-metallic inclusion particles invited the occurrence of defects such as scratches during the production process of the steel material and the steel products, and invited also defects in quality such as the reduction of service life of the steel products. When means for plastic working was different and when the kind of steel products was different, the sizes of the non-metallic inclusion particles that invited the occurrence of defects such as flaws and defects in quality changed, as well. In other words, there was the case where only the non-metallic inclusion particles greater than the seven kinds invited the occurrence of the defects but the non-metallic inclusion particles smaller than the seven kinds did not invite the defects, in accordance with the means for plastic working and the kinds of the steel products.

In this case, it was not necessary to measure the occurring quantity of the non-metallic inclusion particles smaller than the seven kinds. Therefore, the cold crucible treatment was carried out by setting $t/\sqrt{(30\ d)}$ to 4, for example, and cleanliness of the metal could be evaluated by measuring the quantity N pcs/kg of the seven kinds of non-metallic inclusion particles. In this case, it was not necessary, either, to measure eight kinds of non-metallic inclusion particles occurring in greater quantities than the seven kinds, measurement of cleanliness of the metal could be simplified and could be made easier than the prior art method.

Example 6

The present inventors collected samples from continuous cast slabs of low carbon aluminum killed steels having three different kinds of charges and a thickness of 250 mm, and each of the samples was levitation-melted by using a cold crucible having a maximum inner diameter of 30 mm in an Ar atmosphere at atmospheric pressure. The levitation-melted metal was retained for 120 seconds so as to gather the non-metallic inclusions on the surface of the levitation-melted metal, and then the high frequency current applied to the coil of the cold crucible was cut off. Ten and fifteen seconds later from cut-off of the high frequency current, the upper surface of the metal inside the crucible was photographed by a CCD camera. In this instance, the occupying portion of the non-metallic inclusions was formed in an island-form on the upper surface of the metal, and the occupying portion of the non-metallic inclusions was photographed as the image of the islands due to the difference of luminance between the metal and the island-like non-metallic inclusions. This image was subjected to image processing so as to determine the areas of the occupying portions of the non-metallic inclusions.

Each metal sample having the non-metallic inclusions accumulating on the surface thereof inside the crucible was photographed by the CCD camera, and was taken out from the crucible after solidification. After the areas of the occupying portions of the island-like non-metallic inclusions were measured at normal temperature, the metal sample was set as an anode into a 10% acetyl-acetone type electrolyte solution, and the metal surface was electrolyzed to a weight of 0.5 g at a current density of 5 to 50 mA/cm$^2$. After filtration, the weight of the non-metallic inclusions was measured.

The present inventors collected samples from continuous cast slabs of low carbon aluminum killed steels having three different charges, and each sample was levitation-melted by using a crucible having a maximum inner diameter of 100 mm in an Ar atmosphere at the atmospheric pressure. After the non-metallic inclusions were accumulated on the surface of the levitation-melted metal by retaining the levitation-melted metal for 400 seconds, the high frequency current to the coil of the cold crucible was cut off. Ten to fifteen seconds after the cut-off of the high frequency current, the upper surface of the metal inside the crucible was photographed by a CCD camera.

The images so obtained were subjected to image processing in the same way as when the crucible had the maximum inner diameter of 30 mm, and the areas of the occupying portions of the island-like non-metallic inclusions were determined. The metal having the non-metallic inclusions gathering on the surface thereof inside the crucible was subjected to measurement of the occupying areas of the island-like non-metallic inclusions in the same way as when the crucible had the maximum inner diameter of 30 mm, and then the surface of the metal was electrolyzed to a weight of 1 g so as to measure the weight of the non-metallic inclusions.

Figure 3:
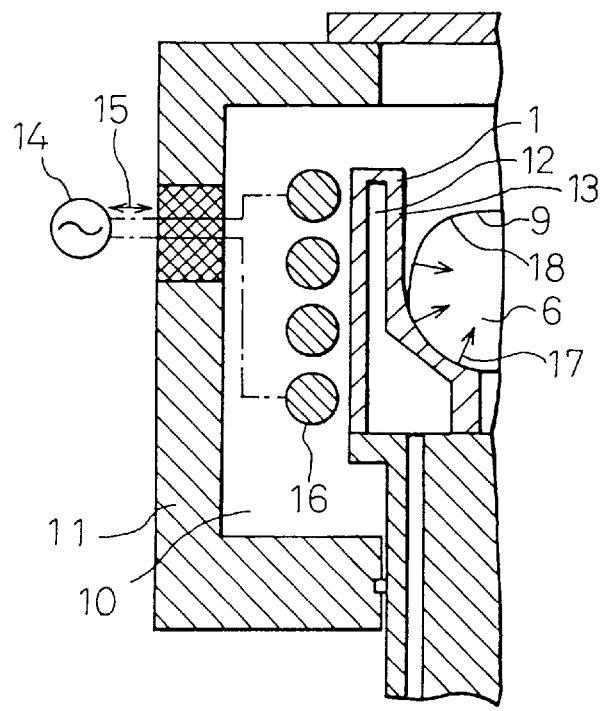
FIG. 3 is an explanatory view showing the crucible shape of the cold crucible apparatus.

FIG. 3 shows the results of these experiments.

TABLE 3

| No. | Maximum inner diameter of crucible (mm) | Occupying area of island-like non-metallic inclusions occupation area (mm$^2$) | | | Weight of non-metallic inclusions obtained by electrolysis (mg) |
|---|---|---|---|---|---|
| | | Time from current cut-off | | After solidification | |
| | | 10 second (a) | 15 second (b) | (c) | (d) |
| 1 | 30 | 201 | 201 | 176 | 25 |
| 2 | 30 | 264 | 176 | 176 | 26 |
| 3 | 30 | 327 | 138 | 113 | 14 |
| 4 | 100 | 477 | 402 | 377 | 60 |
| 5 | 100 | 590 | 465 | 465 | 70 |
| 6 | 100 | 691 | 427 | 377 | 53 |

Figure 21:
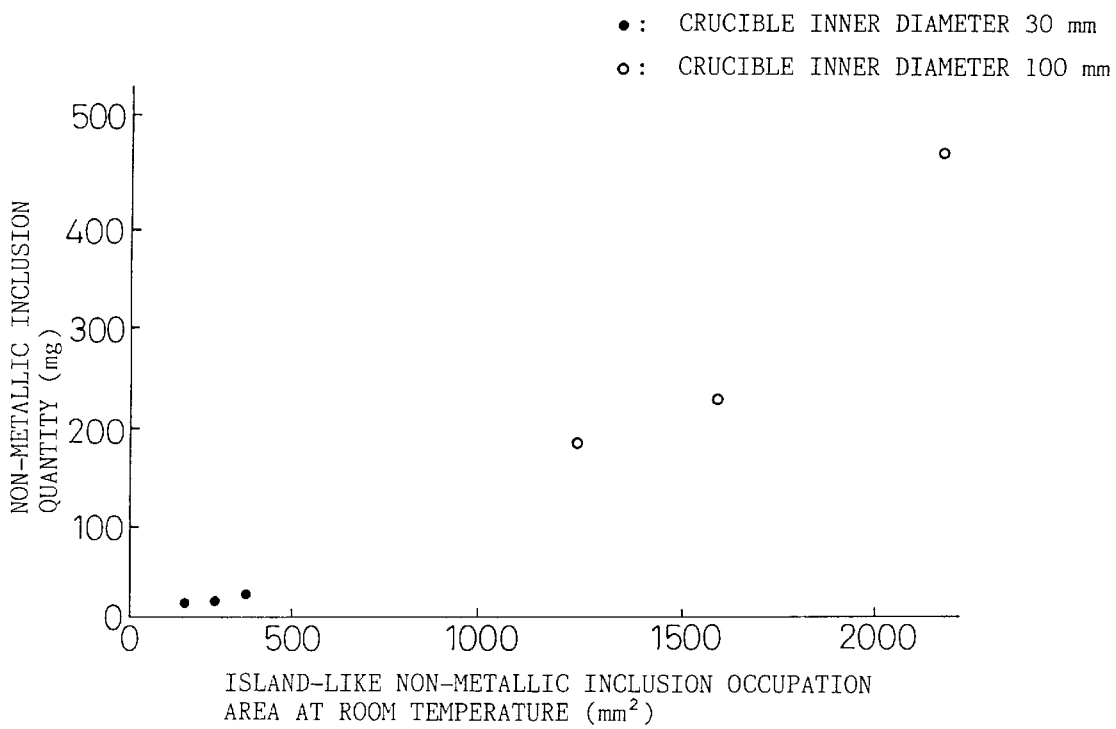
FIG. 21 is a diagram showing the relation between an occupation ratio of island-like non-metallic inclusions after solidification shown in Table 3 and the quantity of non-metallic inclusions.

As can be seen from Table 3, the occupying area of the island-like non-metallic inclusions was great when the time from cut-off of the current was 10 seconds (a in Table 3) but dropped with the passage of time and reached the smallest value after solidification (c in Table 3). FIG. 21 shows the occupying area of the island-like inclusions after solidification (c in Table 3) and the quantity of the non-metallic inclusions obtained by electrolysis (d in Table 3). As can be seen from FIG. 21, the occupying area of the island-like inclusions after solidification had a close correlationship with the quantity of the non-metallic inclusions obtained by electrolytic extraction. Therefore, evaluation of the quantity of the non-metallic inclusions could be made by measuring the occupying area of the island-like non-metallic inclusions after solidification without conducting troublesome electrolytic extraction.

Figure 22:
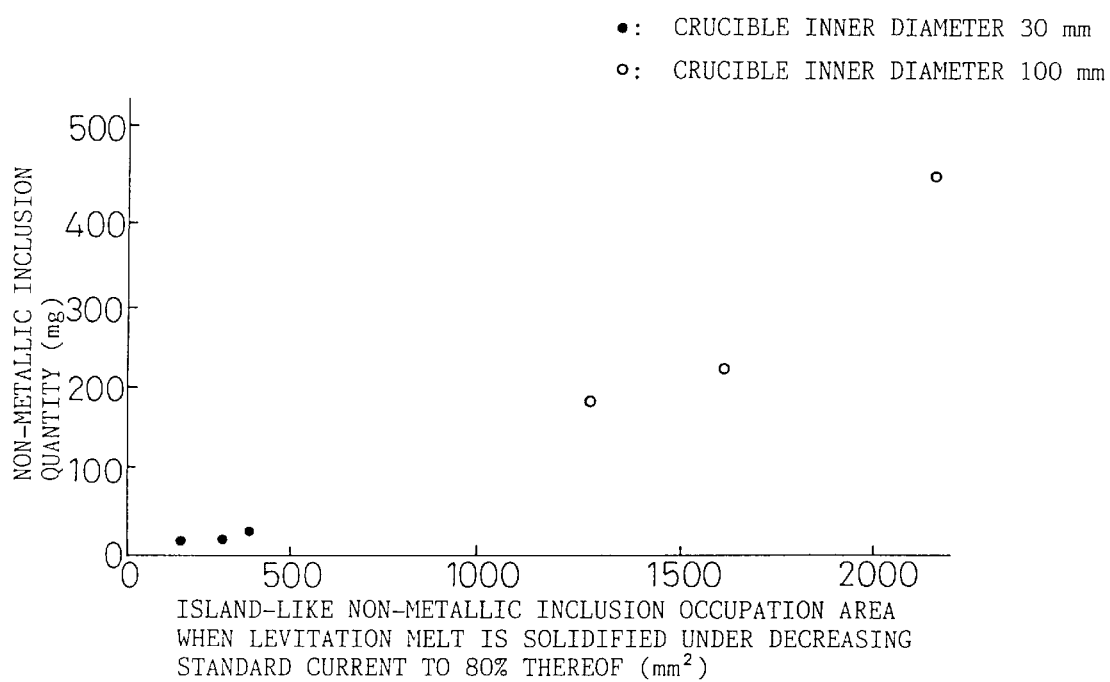
FIG. 22 is a diagram showing the relation between an occupation ratio of island-like non-metallic inclusions at 15 seconds from cut-off of a current solidified by reducing a current of 80% of a reference current and shown in Table 3 and the quantity of non-metallic inclusions.

FIG. 22 is a diagram showing the relation between the occupying area of the island-like non-metallic inclusions after the passage of 15 seconds from cut-off of the current in Table 3 (d in Table 3) and the quantity of the non-metallic inclusions obtained by electrolysis (d in Table 3). Fluctuation was great in FIG. 22 in comparison with FIG. 21 but the occupying area of the island-like non-metallic inclusions after the passage of 15 seconds from cut-off of the current, too, had a close correlation with the quantity of the non-metallic inclusions obtained by electrolytic extraction. Therefore, the occupying portion of the island-like non-metallic inclusions formed on the upper surface of the metal inside the crucible after the passage of 15 seconds from cut-off of the current was photographed without awaiting the solidification of the sample, and the occupying area of the non-metallic inclusions could be measured by image-processing the image of the difference of luminance between the metal and the island-like non-metallic inclusions. In this way, an evaluation could be made.

Figure 23:
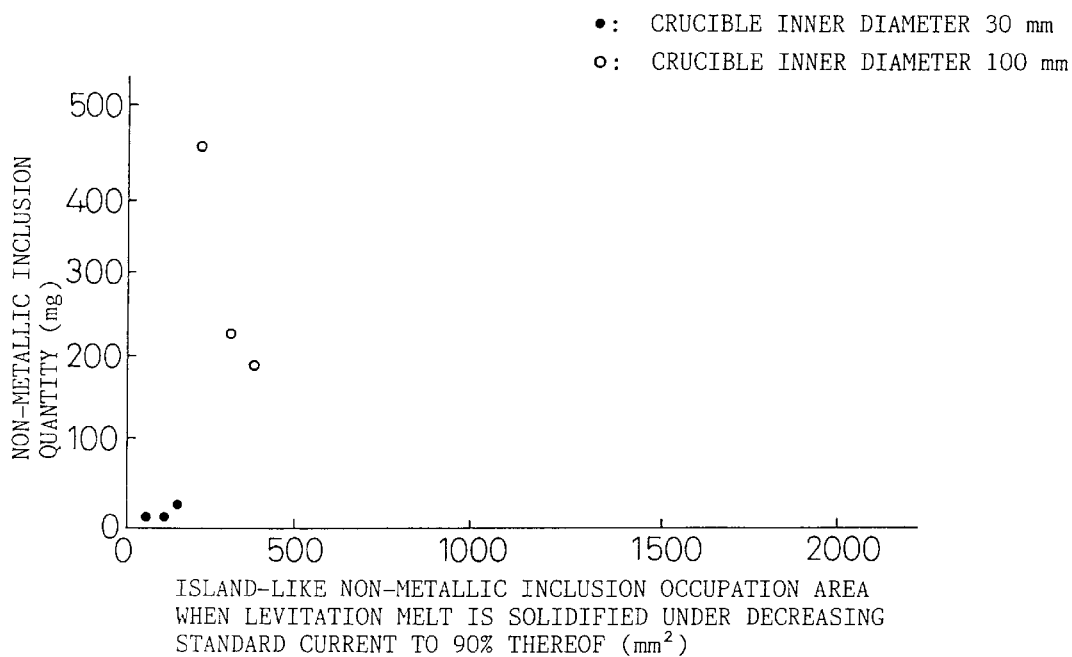
FIG. 23 is a diagram showing the relation between an occupation ratio of island-like non-metallic inclusions at 15 second from cut-off of a current solidified by reducing a current to 90% of a reference current and shown in Table 3 and the quantity of non-metallic inclusions.

FIG. 23 is a diagram showing the relation between the occupying area of the island-like non-metallic inclusions after the passage of 10 seconds from cut-off of the current in Table 3 (a in Table 3) and the quantity of the non-metallic inclusions obtained by electrolysis (d in Table 3). As can be seen from FIG. 23, a high correlationship did not exist between the occupying area of the island-like non-metallic inclusions and the quantity of the non-metallic inclusions after the passage of 10 seconds from cut-off of the current. Therefore, the occupying area of the island-like non-metallic inclusions after the passage of 10 seconds from cut-off of the current was not suitable as a scale for evaluating the quantity of the non-metallic inclusions. For these reasons, the present invention did not use the occupying area of the island-like non-metallic inclusions after the passage of time less than 15 seconds from cut-off of the current for evaluating cleanness of the metal, but exclusively used the occupying area of the island-like non-metallic inclusions after the passage of at least 15 seconds from cut-off of the current for evaluating cleanliness of the metal.

According to the observation of the present inventors, gathering of the non-metallic inclusions to the surface of the levitation-melted metal was not sufficient when the ratio $t/\sqrt{(30\ d)}$ of the retention time t (second) of the levitation-melted metal in the cold crucible and the maximum inner diameter d (mm) of the crucible was less than 1. When $t/\sqrt{(30\ d)}$ was set to 1, large non-metallic inclusions having sizes of about 300 $\mu$m accumulated on the surface of the molten metal. The non-metallic inclusions having the sizes of about 300 $\mu$m invited defects of the steel material and the steel products during their production and use in many cases. Therefore, $t/\sqrt{(30\ d)}$ was preferably set to at least 1 when managing the non-metallic inclusions. When $t/\sqrt{(30\ d)}$ was set to a value greater than 1, small non-metallic inclusions, too, gathered on the surface of the levitation-melted metal with the increase of $t/\sqrt{(30\ d)}$. Even when $t/\sqrt{(30\ d)}$ was set to a value exceeding 20, however, the non-metallic inclusions gathering on the surface of the levitation-melted metal did not further increase. Therefore, the retention time t of the levitation-melted metal was preferably limited to the range of $1 \leq t/\sqrt{(30\ d)} \leq 20$.

FIGS. 7(a) and (b) are explanatory views useful for explaining the movement of the non-metallic inclusions gathering on the surface of the levitation-melted metal. FIG. 7(a) is a schematic view when the high frequency current was caused to flow through the coil to hold the levitation-melted metal. In this case, a gentle stream 10 of the molten metal which rose at the center and flowed along the surface was formed inside the molten metal 4 that was levitated. Due to this stream 10 of the molten metal, the non-metallic inclusions 9 gathering on the surface of the molten metal were caused to flow towards the segments 1 and moved towards them. When the high frequency current was cut off, the stream 10 of this molten metal disappeared, too, and the non-metallic inclusions that had moved towards the segments 1 moved back to the center and formed portions of the island-like non-metallic inclusions as shown in FIG. 7(b). The reason why the occupying area of the island-like non-metallic inclusions after the passage of 10 seconds from cut-off of the current is broadest in Table 3 (a in Table 3) was presumably because the non-metallic inclusions on the segment side 1 were moving towards the center when the time from the cut-off of the current was 10 seconds, gathering of the non-metallic inclusions was not yet sufficient and the non-metallic inclusions were scattered on the surface of the molten metal 4.

Example 7

Metal samples were collected from two adjacent portions 30 mm beneath the skin of continuous cast slabs of a low carbon aluminum killed steels having a thickness of 250 mm. One of the samples was levitation-melted as a Comparative Example by a conventional apparatus having a single-phase high frequency induction heating coil, and the other was levitation-melted by an apparatus having three-phase A.C. induction heating coil as an Example of the present invention. The supply of the current was stopped after the passage of 10 seconds from melting, and each metal sample was cooled to room temperature. The crucible used had a maximum diameter of 30 mm, and power supplied was 30 KVA in both cases and the high frequency was 100 KHz in both cases, too.

To evaluate the degree of accumulating of the non-metallic inclusions to the top portion, the following evaluation was carried out.

The metal sample that was cooled to room temperature was set as an anode into a 10% acetylacetone type electrolyte solution, and the metal surface was electrolyzed at a current density of 5 to 50 mA/cm$^2$. In either case, the metal surface on the top side of the levitation-melted metal was electrolyzed as the first step, and then the whole metal surface was electrolyzed as the second step. The solution used for this electrolysis was filtrated, and the non-metallic inclusions were fractioned and their weight was measured.

The sum of the quantity of the non-metallic inclusions of the first step and that of the second step in Example of the present invention was substantially equal to the sum of the quantities of the first and second steps in Comparative Examples. However, the quantity of the non-metallic inclusions of the first step in the Examples of the present invention was about 95% of the sum of the quantities of the non-metallic inclusions, whereas the quantity of the non-metallic inclusions of the first step was about 60% of the sum in the Comparative Examples. In other words, since the non-metallic inclusions accumulated on the top portion side of the levitation-melted metal in the Examples of the present invention, substantially the whole quantity of the non-metallic inclusions were extracted by electrolysis of the first step. Therefore, the second step could be omitted, and the quantity of the non-metallic inclusions could be measured more quickly and more easily than in the prior art methods. On the other hand, since the non-metallic inclusions were scattered on the entire surface in Comparative Example, the quantity of the non-metallic inclusions extracted by electrolysis of the first step was about 60%, and the second step was essentially necessary.

In other words, the evaluation method of cleanliness of the metal according to the present invention was the method which used the cold crucible having the induction heating coil using the three-phase A.C. high frequency current, formed the upward stream on the surface of the molten metal which was levitation-melted, caused the non-metallic inclusions discharged to gather on the surface of the top portion of the molten metal, measured the non-metallic inclusions so accumulating on the top portion of the molten metal, and evaluated cleanliness of the metal by this measured value.

The present inventors further collected samples from continuous cast slabs of three low carbon aluminum killed steels having mutually different charges, and levitation-melted them by the apparatus having the three-phase A.C. induction heating coil of the present invention. After each sample was held under the levitation-melted state for about 10 seconds, the supply of power was stopped, and the top portion of each metal sample during cooling was photographed by the CCD camera. Because luminance of the metal during cooling was different from that of the non-metallic inclusions, an image wherein the island-like occupying zones of the non-metallic inclusions were formed at the center could be obtained in each case. The area of the occupying zones of the non-metallic inclusions was measured by processing the image so obtained.

Figure 24:
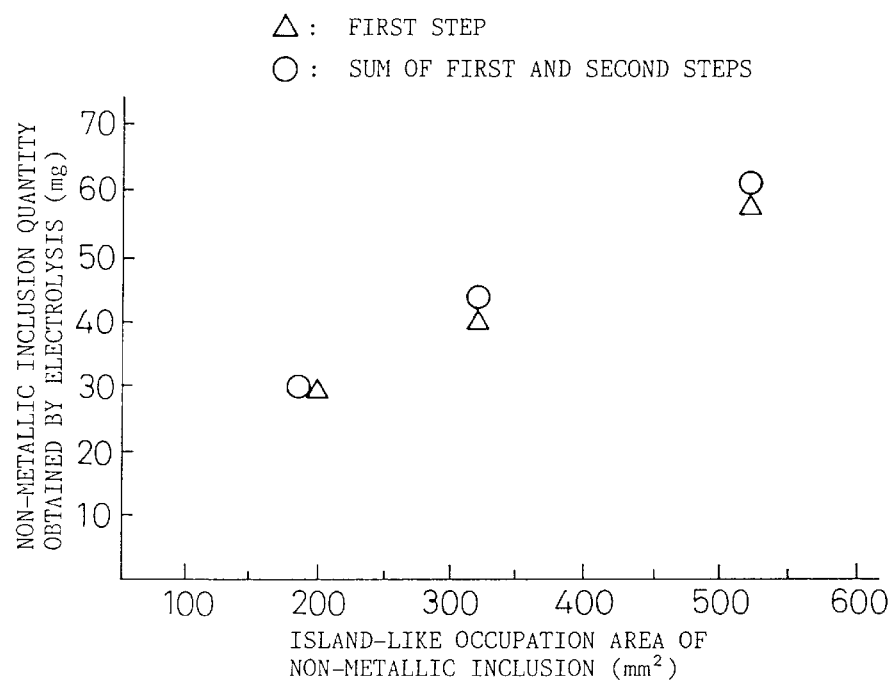
FIG. 24 is a diagram showing the relation between an occupation ratio of non-metallic inclusions by a surface electrolysis method and the quantity of non-metallic inclusions.

Each metal sample was cooled to room temperature, and the metal surface was electrolyzed in the same way as described above. Thereafter, the weight of the non-metallic inclusions was measured. FIG. 24 is a diagram showing the relation between the area of the island-like occupying zones of the non-metallic inclusions and the quantity of the non-metallic inclusions obtained by the electrolytic method. As can be seen from FIG. 24, an extremely close correlationship could be observed between them. When the quantity of the non-metallic inclusions was measured by the electrolytic method, cooling, electrolysis, filtration, weighing, etc., of the metal sample were necessary, the processing was complicated, and the processing time was long. When the area of the island-like occupying zones of the non-metallic inclusions was measured, on the other hand, the processing was extremely simple, and could be conducted within an extremely short time. Therefore, the present invention measured the island-like occupying area of the non-metallic inclusions and evaluated the quantity of the non-metallic inclusions by this area. The method of measuring the island-like occupying area of the non-metallic inclusions provided the highest accuracy, was easy to practice quickly, and was extremely suitable when the non-metallic inclusions were used as a guideline for the production or use of the steel materials.

Example 8

Casting samples were collected from a molten steel of a low carbon steel inside a tundish during casting by a continuous casting machine, and rectangular samples having a weight of 100 g were cut out. Each sample was then molten by using a cold crucible apparatus in an Ar atmosphere at the atmospheric pressure, was retained for 5 minutes after solidification and was solidified after inclusions were discharged.

The surface of each sample molten by the cold crucible was analyzed by fluorescent X-rays. Measurement was carried out at a primary X-ray intensity of 1 $\mu A \times 50$ kV and an irradiation time of 90 seconds. Existence indexes of alumina, silicate, calcia, etc., were determined from the fluorescent X-ray intensity of Al, Si, Ca, etc.

Each sample melted in the cold crucible was fixed between sample holder pads of a sample rotating apparatus in such a manner as to freely rotate the sample round the center axis, and while the sample was being rotated at 6 rpm, the fluorescent X-ray analysis was conducted. The results were tabulated in Table 4. Table 4 shows also the results when the sample under the stationary state was measured while the direction of the sample was changed, without using the sample rotating apparatus, as a Comparative Example.

TABLE 4

| | | Alumina index | | Calcia index | |
|---|---|---|---|---|---|
| Sample No. | Measurement plane | This Invention | Comparative Example | This Invention | Comparative Example |
| 1 | Measurement plane 1 | | 4.0 | | 0.003 |
| | 2 | | 6.3 | | 0.006 |
| | 3 | | 13.1 | | 0.007 |
| | 4 | | 7.1 | | 0.006 |
| | | 8.2 | mean 7.6 | 0.005 | mean 0.006 |
| 2 | Measurement plane 1 | | 10.1 | | 0.007 |
| | 2 | | 21.0 | | 0.002 |
| | 3 | | 13.7 | | 0.003 |
| | 4 | | 4.9 | | 0.002 |
| | | 11.7 | mean 12.4 | 0.006 | mean 0.006 |
| 3 | Measurement plane 1 | | mean 18.4 | | 0.328 |
| | 2 | | 16.8 | | 0.750 |
| | 3 | | 4.6 | | 0.157 |
| | 4 | | 4.4 | | 0.071 |
| | | 11.5 | mean 11.0 | 0.339 | mean 0.326 |
| 4 | Measurement plane 1 | | 33.2 | | 0.677 |
| | 2 | | 20.2 | | 0.210 |
| | 3 | | 17.9 | | 0.408 |
| | 4 | | 23.1 | | 0.682 |
| | | 25.4 | mean 23.6 | 0.488 | 0.494 |

As can be understood from this Comparative Example, significant variance existed in the distribution of the non-metallic inclusions depending on the measurement surface, and the correct result could not be obtained unless the entire periphery of the side surface of the sample was measured. The result by the present invention substantially agreed with the mean value of the measurement values of the four surfaces of Comparative Example, and this indicated that the present invention could be used as the index of the non-metallic inclusions. On the other hand, the evaluation time per sample according to the present invention was three minutes, and an evaluation speed of about ⅓ of that of Comparative Example could be accomplished. Even when the measurement of the four surfaces of Comparative Example was carried out by using the interrupted rotation mode of the sample rotating apparatus of the present invention, the evaluation time could be reduced by about 40%.

INDUSTRIAL APPLICABILITY

As described above, the method of the present invention can analyze and evaluate quickly and economically the non-metallic inclusions in the metal while keeping good representativity and correlation with the product. Quick evaluation of the inclusions by the present method can be applied as a management index of the steel making operation when intermediate products are forwarded to subsequent steps to guarantee quality, or as an evaluation index when a new process is developed and introduced.

We claim:

1. An evaluation method for cleanliness of a metal piece comprising the steps of:

levitation-melting said metal piece for a predetermined time by using levitation-melting means thereby forming molten metal on a surface of said metal piece;

discharging non-metallic inclusions contained in said metal piece to said molten metal formed on said surface of said metal piece by said levitation melting;

solidifying the molten metal on the surface of said metal piece;

directly analyzing by a fluorescent X-ray analysis method a curved and non-smooth surface of said metal piece after solidification by using an energy dispersion type spectroscope so as to measure quantities of elements constituting said non-metallic inclusions and identifying the quantities of said non-metallic inclusions.

2. An evaluation method for cleanliness of a metal piece according to claim 1, further comprising:

after said solidifying step and during said direct analyzing, rotating either intermittently or continuously said metal piece having the curved and non-smooth surface around an axis connecting an uppermost point and a lowermost point during melting as a center thereof; and said identifying step further includes identifying quantities of said non-metallic inclusions in accordance with kind and type.

* * * * *

UNITED STATES PATENT AND TRADEMARK OFFICE
CERTIFICATE OF CORRECTION

PATENT NO. : 5,985,674
DATED : November 16, 1999
INVENTOR(S) : Kazushige UMEZAWA, et al.

It is certified that error appears in the above-identified patent and that said Letters Patent is hereby corrected as shown below:

Title page, item [30], last line under "Foreign Application Priority Data", change "May 19, 1999" to May 19, 1995-.

Signed and Sealed this

Seventeenth Day of April, 2001

Attest:

NICHOLAS P. GODICI

*Attesting Officer*  *Acting Director of the United States Patent and Trademark Office*